US008859490B2

(12) United States Patent
Liu et al.

(10) Patent No.: US 8,859,490 B2
(45) Date of Patent: Oct. 14, 2014

(54) PEPTIDE NUCLEIC ACID MONOMERS AND OLIGOMERS

(75) Inventors: Chuan Fa Liu, Singapore (SG); Yun Zeng, Singapore (SG); Xiao Wei Lu, Singapore (SG)

(73) Assignee: Nanyang Technological University, Singapore (SG)

( * ) Notice: Subject to any disclaimer, the term of this patent is extended or adjusted under 35 U.S.C. 154(b) by 582 days.

(21) Appl. No.: 13/062,194

(22) PCT Filed: Sep. 3, 2008

(86) PCT No.: PCT/SG2008/000324
§ 371 (c)(1),
(2), (4) Date: Jun. 22, 2011

(87) PCT Pub. No.: WO2010/027326
PCT Pub. Date: Mar. 11, 2010

(65) Prior Publication Data
US 2011/0245458 A1 Oct. 6, 2011
US 2012/0065364 A2 Mar. 15, 2012

(51) Int. Cl.
C07K 2/00 (2006.01)
C07D 239/47 (2006.01)
C07D 239/54 (2006.01)
C07D 473/18 (2006.01)
C07D 473/34 (2006.01)
C07D 239/60 (2006.01)
C07K 14/00 (2006.01)
C07D 239/557 (2006.01)

(52) U.S. Cl.
CPC .......... *C07D 239/557* (2013.01); *C07D 473/34* (2013.01); *C07D 473/18* (2013.01); *C07D 239/60* (2013.01); *C07K 14/003* (2013.01)
USPC ........... 514/1.1; 514/3.2; 514/256; 514/263.1

(58) Field of Classification Search
None
See application file for complete search history.

(56) References Cited

U.S. PATENT DOCUMENTS

| 5,786,461 | A | * | 7/1998 | Buchardt et al. | ............. 536/18.7 |
| 6,133,444 | A | * | 10/2000 | Coull et al. | .................... 544/276 |
| 2007/0003966 | A1 | | 1/2007 | Dey et al. | ............................ 435/6 |

FOREIGN PATENT DOCUMENTS

WO  92/20702  11/1992

OTHER PUBLICATIONS

Maison et al., Multicomponent Synthesis of Novel Amino Acid-Nucleobase Chimeras: a Versatile Approach to PNA-Monomers, Bioorganic & Medicinal Chemistry 8 (2000) 1343-1360.*

Zhou et al., Novel Binding and Efficient Cellular Uptake of Guanidine-Based Peptide Nucleic Acids (GPNA), JACS, 2003, 125, 6878-6879.*
Demidov et al., "Stability of peptide nucleic acids in human serum and cellular extracts," *Biochemical Pharmacology* 48(6):1310-1313, 1994.
Dragulescu-Andrasi et al., "A Simple γ-Backbone Modification Preorganizes Peptide Nucleic Acid into a Helical Structure," *J. Am. Chem. Soc.* 128:10258-10267, 2006.
Dragulescu-Andrasi et al., "Cell-permeable GPNA with appropriate backbone stereochemistry and spacing binds sequence-specifically to RNA," *Chem. Commun*, pp. 244-246, 2005.
Efimov et al., "Polyester and N-Methyl Analogues of Peptide Nucleic Acids: Synthesis and Hybridization Properties," *Nucleosides & Nucleotides* 18(11&12):2533-2549, 1999.
Egholm et al., "PNA hybridizes to complementary oligonucleotides obeying the Watson-Crick hydrogen- bonding rules," *Nature* 365:566-568, 1993.
Englund et al., "γ-Substituted Peptide Nucleic Acids Constructed from L-Lysine are a Versatile Scaffold for Multifunctional Display," *Angew. Chem. Int. Ed.* 46:1414-1418, 2007.
Finn et al., "Synthesis and properties of DNA-PNA chimeric oligomers," *Nucleic Acids Research* 24(17):3357-3363, 1996.
Haaima et al., "Peptide Nucleic Acids (PNAs) Containing Thymine Monomers Derived from Chiral Amino Acids: Hybridization and Solubility Properties of D-Lysine PNA," *Angew. Chem. Int. Ed. Engl.* 35(17):1939-1942, 1996.
Haaima et al., "Peptide nucleic acids (PNAs) derived from N-(N-methylaminoethyl)glycine. Synthesis, hybridization and structural properties," *New J. Chem.* 23:833-840, 1999.
Hudson et al., "PNA-Directed Triple-Helix Formation by $N^7$-Xanthine," *Synlett* 9:1442-1446, 2005.
Hyrup et al., "Structure-Activity Studies of the Binding of Modified Peptide Nucleic Acids (PNAs) to DNA," *J. Am. Chem. Soc.* 116:7964-7970, 1994.
Janowski et al., "Inhibiting transcription of chromosomal DNA with antigene peptide nucleic acids," *Nature Chemical Biology* 1(4):210-215, 2005.
Janowski et al., "Silencing gene expression by targeting chromosomal DNA with antigene peptide nucleic acids and duplex RNAs," *Nature Protocols* 1(1):436-443, 2006.
Knudsen et al., "Application of peptide nucleic acid in cancer therapy," *Anti-Cancer Drugs* 8:113-118, 1997.
Koppelhus et al., "Cellular delivery of peptide nucleic acid (PNA)," *Advanced Drug Delivery Reviews* 55:267-280, 2003.

(Continued)

Primary Examiner — Maury Audet
Assistant Examiner — Joseph Fischer
(74) Attorney, Agent, or Firm — Seed IP Law Group PLLC

(57) ABSTRACT

Disclosed is a peptide nucleic acid monomer as well as a corresponding peptide nucleic acid molecule. The monomer comprises a terminal amino group and a terminal group A. The terminal amino group and the terminal group A are connected by an aliphatic moiety. The main chain of this aliphatic moiety is free of groups that are charged under physiological conditions. The terminal group A is one of —COOH, —COOR$^3$, —COX, —COSR$^3$, —CN, —CONH$_2$, —CONHR$^3$, —CONR$^3$, R$^4$, with R$^3$ and R4 being H or an aliphatic, alicyclic, aromatic, arylaliphatic or arylalicyclic group, and X being a halogen atom. The terminal amino group is substituted by an aliphatic group with a main chain of at least two carbon atoms and optionally 0 to about 2 heteroatoms selected from the group N, O, S, Se and Si. The main chain has a polar head group Z.

12 Claims, 13 Drawing Sheets

(56) References Cited

OTHER PUBLICATIONS

Kumar et al., "Conformationally Constrained PNA Analogues: Structural Evolution toward DNA/RNA Binding Selectivity," *Acc. Chem. Res. 38*:404-412, 2005.

Liu et al., "Characterization of TectoRNA Assembly with Cationic Conjugated Polymers," *J. Am. Chem. Soc. 126*:4076-4077, 2004.

Meier et al., "Peptide Nucleic Acids (PNAs)-Unusual Properties of Nonionic Oligonucleotide Analogues," *Angew. Chem. Int. Ed. Engl. 31*(8):1008-1010, 1992.

Muller et al., "Building Units for N-Backbone Cyclic Peptides. 3. Synthesis of Protected $N^\alpha$-(ω-Aminoalkyl)amino Acids and $N^\alpha$-(ω-Carboxyalkyl)amino Acids," *J. Org. Chem. 62*:411-416, 1997.

Nagahara et al., "Transduction of full-length TAT fusion proteins into mammalian cells: TAT-p27$^{Kip1}$ induces cell migration," *Nature Medicine 4*(12):1449-1452, published 1998.

Nielsen et al., "Sequence-Selective Recognition of DNA by Strand Displacement with a Thymine-Substituted Polyamide," *Science 254*(5037):1497-1500, 1991.

Osterman et al., "Regiochemical Assignment of Methylated Purines and Pyrimidines by Selective INEPT," *Tetrahedron Letters 33*(34):4867-4870, 1992.

Sforza et al., "Chiral Peptide Nucleic Acids (PNAs): Helix Handedness and DNA Recognition," *Eur. J. Org. Chem.*, pp. 197-204, 1999.

Sforza et al., "Role of Chirality and Optical Purity in Nucleic Acid Recognition by PNA and PNA Analogs," *Chirality 14*:591-598, 2002.

Shakeel et al., "Peptide nucleic acid (PNA)—a review," *J. Chem. Technol. Biotechnol. 81*:892-899, 2006.

Shiraishi et al., "Enhanced delivery of cell-penetrating peptide-peptide nucleic acid conjugates by endosomal disruption," *Nature Protocols 1*(2):1-4, 2006.

Thomson et al., "Fmoc Mediated Synthesis of Peptide Nucleic Acids," *Tetrahedron 51*(22):6179-6194, 1995.

Timár et al., "Fmoc/Acyl protecting groups in the synthesis of polyamide (peptide) nucleic acid monomers," *J. Chem. Soc., Perkin Trans. 1*:19-26, 2000.

Wender et al., "The design, synthesis, and evaluation of molecules that enable or enhance cellular uptake: Peptoid molecular transporters," *PNAS 97*(24):13003-13008, 2000.

Will et al., "The Synthesis of Polyamide Nucleic Acids using a Novel Monomethoxytrityl Protecting-Group Strategy," *Tetrahedron 51*(44):12069-12082, 1995.

Wojciechowski et al., "Nucleobase Modifications in Peptide Nucleic Acids," *Current Topics in Medicinal Chemistry 7*:667-679, 2007.

Yamamoto et al., "Highly efficient strand invasion by peptide nucleic acid bearing optically pure lysine residues in its backbone," *Nucleic Acids Symposium Series No. 50*:109-110, 2006.

Zhou et al., "Novel Binding and Efficient Cellular Uptake of Guanidine-Based Peptide Nucleic Acids (GPNA)," *J. Am. Chem. Soc. 125*:6878-6879, 2003.

\* cited by examiner

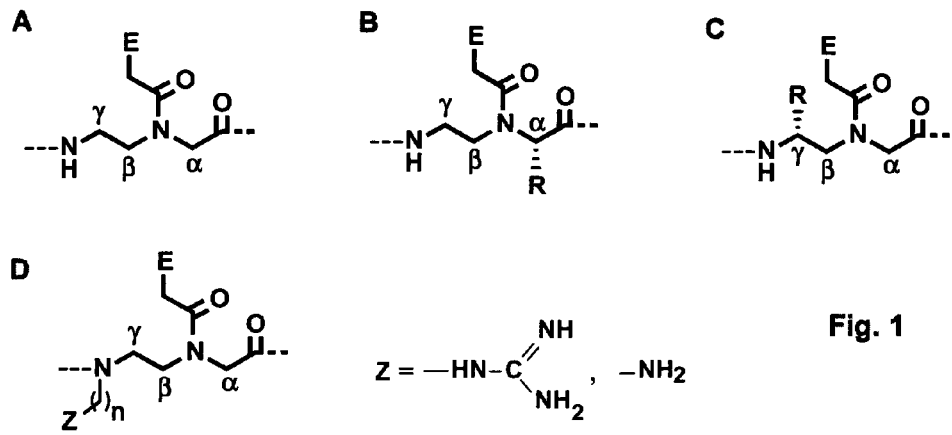
Fig. 1
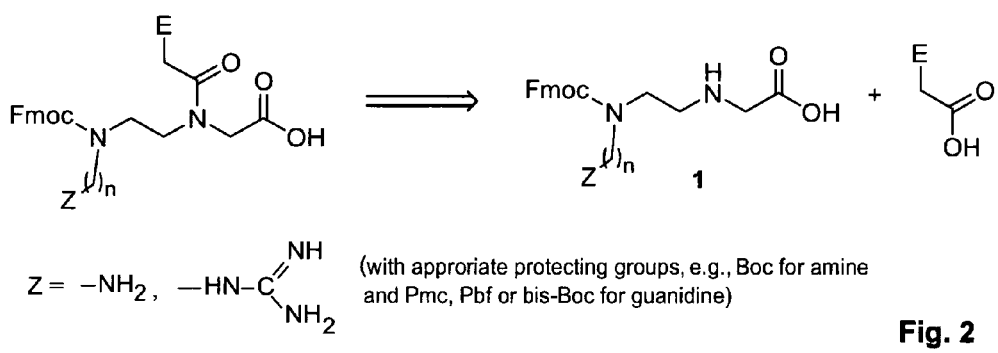
Fig. 2
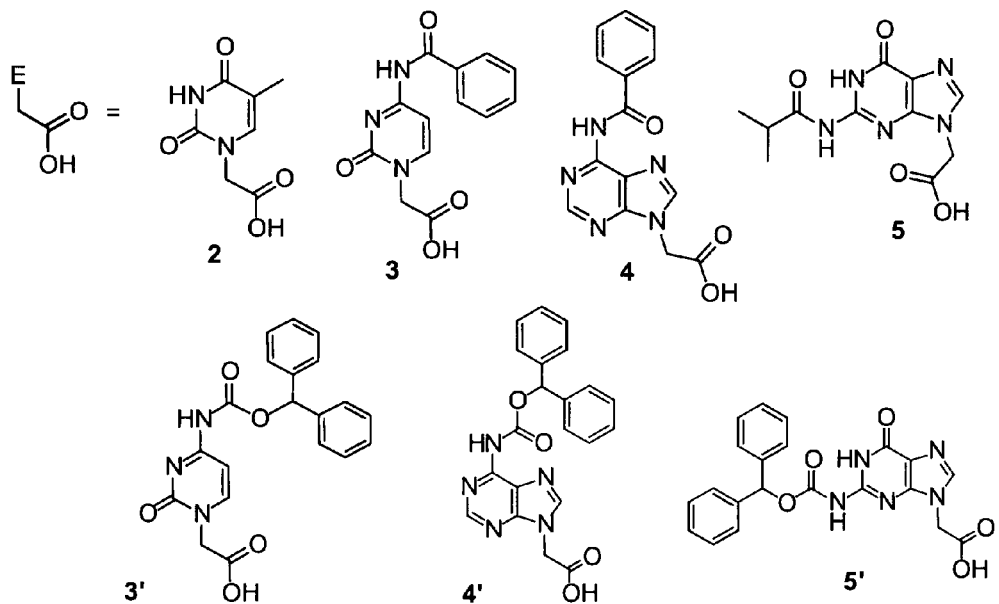

Fig. 7A PNAs containing peptoid side chains with a 6-C spacer

| | Sequence | Anti-parallel DNA duplex[a] | Parallel DNA duplex[b] | Mismatch DNA duplex[c] |
|---|---|---|---|---|
| aegPNA | Ac-GTAGATCACT-Gly-NH$_2$ | 48.55 | 34.89 | 36.37[e] |
| AP-PNA 6-1 | Ac-GTAGAT$^{6a}$CACT-Gly-NH$_2$ | 48.96(+0.41)[d] | 37.20 | 33.83[e] |
| Ac-AP-PNA 6-1 | Ac-GTAGAT$^{6a(Ac)}$CACT-Gly-NH$_2$ | 47.56(-0.99)[d] | 38.94 | 41.60[e] |
| AP-PNA 6-2 | Ac-GTAGA$^{6a}$T$C^{6a}$ACT-Gly-NH$_2$ | 47(-1.55)[d] | 36.89 | 31.70[e] |
| Ac-AP-PNA 6-2 | Ac-GTAGA$^{6a(Ac)}$T$C^{6a(Ac)}$ACT-Gly-NH$_2$ | 49.40(+0.85)[d] | 47.56 | ND |
| AP-PNA 6-3 | Ac-G$^{6a}$TAGA$^{6a}$T$C^{6a}$ACT-Gly-NH$_2$ | 46.34(-2.21)[d] | 34.97 | 31.00[e] |
| AP-PNA 6-4 | Ac-GT$^{6a}$AG$^{6a}$AT$^{6a}$CA$^{6a}$CT-Gly-NH$_2$ | 45.84(-2.71)[d] | 35.61 | 34.25[e] |
| AP-PNA 6-5 | Ac-GT$^{6a}$AG$^{6a}$AT$^{6a}$CA$^{6a}$CT$^{6a}$-Gly-NH$_2$ | 46.40(-2.15)[d] | 36.04 | 34.92[e] |
| GP-PNA 6-1 | Ac-GTAGAT$^{6g}$CACT-Gly-NH$_2$ | 48.45(-0.1)[d] | 38.79 | 25.23[e] |
| GP-PNA 6-2 | Ac-GTAGA$^{6g}$T$C^{6g}$ACT-Gly-NH$_2$ | 46.7(-1.85)[d] | 38.13 | 21.60[e] |
| GP-PNA 6-3 | Ac-G$^{6g}$TAGA$^{6g}$T$C^{6g}$ACT-Gly-NH$_2$ | 48.98(+0.43)[d] | 32.22 | 33.43[e] |
| GP-PNA 6-4 | Ac-GT$^{6g}$AG$^{6g}$AT$^{6g}$CA$^{6g}$CT-Gly-NH$_2$ | 47.00(-1.55)[d] | 33.59 | 27.9[e] |
| GP-PNA 6-5 | Ac-GT$^{6g}$AG$^{6g}$AT$^{6g}$CA$^{6g}$CT$^{6g}$-Gly-NH$_2$ | 46.53(-2.02)[d] | 31.98 | 36.19[e] |

[a] 5'd(AGTGATCTAC). [b] 5'd(CATCTAGTGA). [c] 5'd(AGTGGTCTAC). [d] ΔTm. [e] due to a thermal transition of the single stranded PNA itself around 40 °C, this value is difficult to determine accurately.

Fig. 7B PNAs containing peptoid side chains with a 4-C spacer

| | Sequence | Anti-parallel DNA duplex[a] | Parallel DNA duplex[b] | Mismatch DNA duplex[c] |
|---|---|---|---|---|
| aegPNA | Ac-GTAGATCACT-Gly-NH$_2$ | 48.55 | 34.89 | 36.37[e] |
| AP-PNA 4-1 | Ac-GTAGAT[4a]CACT-Gly-NH$_2$ | 46.07(-2.48)[d] | 31.54 | 31.06 |
| AP-PNA 4-2 | Ac-GTAGAT[4a]TC[4a]ACT-Gly-NH$_2$ | 46.64(-1.91)[d] | 34.3 | 31.90 |
| AP-PNA 4-3 | Ac-G[4a]TAGAT[4a]TC[4a]ACT-Gly-NH$_2$ | 45.95(-2.6)[d] | 37.8 | 33.30 |
| AP-PNA-4-4 | Ac-GT[4a]AG[4a]AT[4a]CA[4a]CT-Gly-NH$_2$ | 45.45(-3.1)[d] | 39.4 | 34.60 |
| GP-PNA 4-1 | Ac-GTAGAT[4g]CACT-Gly-NH$_2$ | 48(-0.55)[d] | 33.27 | 33.89 |
| GP-PNA 4-2 | Ac-GTAGAG[4g]TC[4g]ACT-Gly-NH$_2$ | 47.87(-0.68)[d] | 37 | 29.64 |
| GP-PNA 4-3 | Ac-G[4g]TAGAG[4g]TC[4g]ACT-Gly-NH$_2$ | 49.03(+0.48)[d] | 33.88 | 35.84 |
| GP-PNA 4-4 | Ac-GT[4g]AG[4g]AT[4g]CA[4g]CT-Gly-NH$_2$ | 43.97(-4.6)[d] | 32.95 | 33.06 |

[a] 5'd(AGTGATCTAC). [b] 5'd(CATCTAGTGA). [c] 5'd(AGTGGTCTAC). [d] ΔTm. [e] due to a thermal transition of the single stranded PNA itself around 40 °C, this value is difficult to determine accurately.

Fig. 7C PNAs containing peptoid side chains with a 3-C spacer

| | Sequence | Anti-parallel DNA duplex[a] | Parallel DNA duplex[b] | Mismatch DNA duplex[c] |
|---|---|---|---|---|
| aegPNA | Ac-GTAGATCACT-Gly-NH$_2$ | 48.55 | 34.89 | 36.37[e] |
| AP-PNA 3-1 | Ac-GTAGAT$^{3a}$CACT-Gly-NH$_2$ | 43.6(-4.95)[d] | 32.67 | 28.97 |
| AP-PNA 3-2 | Ac-GTAGA$^{3a}$TC$^{3a}$ACT-Gly-NH$_2$ | 40.57(-7.98)[d] | 33.77 | 25.85 |
| AP-PNA 3-3 | Ac-G$^{3a}$TAGA$^{3a}$TC$^{3a}$ACT-Gly-NH$_2$ | 37.34(-11.21)[d] | 33.95 | 23.09 |
| AP-PNA 3-4 | Ac-GT$^{3a}$AG$^{3a}$AT$^{3a}$CA$^{3a}$CT-Gly-NH$_2$ | 30.5(-18.05)[d] | 29.48 | 32.44 |
| GP-PNA 3-1 | Ac-GTAGAT$^{3g}$CACT-Gly-NH$_2$ | 45.43(-3.12)[d] | 31.48 | 31.93 |
| GP-PNA 3-2 | Ac-GTAGA$^{3g}$TC$^{3g}$ACT-Gly-NH$_2$ | 47.99(-0.56)[d] | 30.91 | 22.58 |
| GP-PNA 3-3 | Ac-G$^{3g}$TAGA$^{3g}$TC$^{3g}$ACT-Gly-NH$_2$ | ND | ND | ND |
| GP-PNA 3-4 | Ac-GT$^{3g}$AG$^{3g}$AT$^{3g}$CA$^{3g}$CT-Gly-NH$_2$ | 37.88(-10.67)[d] | 34.96 | 27.00 |

[a] 5'd(AGTGATCTAC). [b] 5'd(CATCTAGTGA). [c] 5'd(AGTGGTCTAC). [d] $\Delta$Tm. [e] due to a thermal transition of the single stranded PNA itself around 40 °C, this value is difficult to determine accurately.

Fig. 7D PNAs containing peptoid side chains with a 2-C spacer

| | Sequence | Anti-parallel DNA duplex[a] | Parallel DNA duplex[b] | Mismatch DNA duplex[c] |
|---|---|---|---|---|
| aegPNA | Ac-GTAGATCACT-Gly-NH$_2$ | 48.55 | 34.89 | 36.37[e] |
| AP-PNA 2-1 | Ac-GTAGAT$^{2a}$CACT-Gly-NH$_2$ | 40.22(-8.33)[d] | 34.39 | 28.92 |
| AP-PNA 2-2 | Ac-GTAGA$^{2a}$TC$^{2a}$ACT-Gly-NH$_2$ | 39.01(-9.54)[d] | 31.93 | 31.59 |
| AP-PNA 2-3 | Ac-G$^{2a}$TAGA$^{2a}$TC$^{2a}$ACT-Gly-NH$_2$ | 36.15(-12.4)[d] | 32.88 | 31.38 |
| AP-PNA 2-4 | Ac-GT$^{2a}$AG$^{2a}$AT$^{2a}$CA$^{2a}$CT-Gly-NH$_2$ | 30.3(-18.25)[d] | 32.06 | 28.97 |
| GP-PNA 2-1 | Ac-GTAGAT$^{2g}$CACT-Gly-NH$_2$ | 41.53(-7.02)[d] | 31.53 | 27.35 |
| GP-PNA 2-2 | Ac-GTAGA$^{2g}$TC$^{2g}$ACT-Gly-NH$_2$ | 39.30(-9.25)[d] | 30.61 | 24.98 |
| GP-PNA 2-3 | Ac-G$^{2g}$TAGA$^{2g}$TC$^{2g}$ACT-Gly-NH$_2$ | 36.82(-11.73)[d] | 35.83 | 27.32 |
| GP-PNA 2-4 | Ac-GT$^{2g}$AG$^{2g}$AT$^{2g}$CA$^{2g}$CT-Gly-NH$_2$ | 33.31(-15.24)[d] | 32.68 | 28.70 |
| βAlaAP-PNA2-1 | Ac-GTAGAT$^{2a(\beta Ala)}$CACT-Gly-NH$_2$ | 45.19 (-3.25)[d] | 32.87 | 32.50 |

[a] 5'd(AGTGATCTAC). [b] 5'd(CATCTAGTGA). [c] 5'd(AGTGGTCTAC). [d] ΔTm. [e] due to a thermal transition of the single stranded PNA itself around 40 °C, this value is difficult to determine accurately.

Fig. 7E Thermal stability (Tm, °C) of examplary PNA-RNA duplexes

|  | Sequence | Anti-parallel RNA[a] duplex | Mismatch RNA[b] duplex |
|---|---|---|---|
| Aeg-PNA | Ac-GTAGATCACT-Gly-NH$_2$ | 51.88 | 42.69 |
| AP-PNA 6-1 | Ac-GTAGAT$^{6a}$CACT-Gly-NH$_2$ | 51.80 | 39.25 |
| AP-PNA 6-2 | Ac-GTAGA$^{6a}$TC$^{6a}$ACT-Gly-NH$_2$ | 52.87 | 43.86 |
| AP-PNA 6-3 | Ac-G$^{6a}$TAGA$^{6a}$TC$^{6a}$ACT-Gly-NH$_2$ | 52.43 | 43.44 |
| AP-PNA 6-4 | Ac-GT$^{6a}$AG$^{6a}$AT$^{6a}$CA$^{6a}$CT-Gly-NH$_2$ | 53.59 | 44.00 |
| AP-PNA 6-5 | Ac-GT$^{6a}$AG$^{6a}$AT$^{6a}$CA$^{6a}$CT$^{6a}$-Gly-NH$_2$ | 54.29 | 44.44 |
| GP-PNA 6-1 | Ac-GTAGAT$^{6g}$CACT-Gly-NH$_2$ | 52.38 | 42.73 |
| GP-PNA 6-2 | Ac-GTAGA$^{6g}$TC$^{6g}$ACT-Gly-NH$_2$ | 52.02 | 44.50 |
| GP-PNA 6-3 | Ac-G$^{6g}$TAGA$^{6g}$TC$^{6g}$ACT-Gly-NH$_2$ | 52.68 | 43.24 |
| GP-PNA 6-4 | Ac-GT$^{6g}$AG$^{6g}$AT$^{6g}$CA$^{6g}$CT-Gly-NH$_2$ | 55.37 | 44.17 |
| GP-PNA 6-5 | Ac-GT$^{6g}$AG$^{6g}$AT$^{6g}$CA$^{6g}$CT$^{6g}$-Gly-NH$_2$ | 54.00 | 43.73 |
| AP-PNA 5-1 | Ac-GTAGAT$^{5a}$CACT-Gly-NH$_2$ | 52.04 | 41.70 |
| AP-PNA 4-1 | Ac-GTAGAT$^{4a}$CACT-Gly-NH$_2$ | 51.51 | 42.22 |
| AP-PNA 3-1 | Ac-GTAGAT$^{3a}$CACT-Gly-NH$_2$ | 50.12 | 40.28 |
| AP-PNA 2-1 | Ac-GTAGAT$^{2a}$CACT-Gly-NH$_2$ | 48.89 | 40.97 |

[a] 5'-AGUGAUCUAC-3'. [b] 5'-AGUG<u>G</u>UCUAC-3'.

Fig. 10

| | Sequence | Expected Mass (isotopic) | Observed m/z [M+H]$^+$ |
|---|---|---|---|
| aegPNA | Ac-GTAGATCACT-Gly-NH$_2$ | 2824.12 | 2826.14 |
| AP-PNA 6-1 | Ac-GTAGAT$^{6a}$CACT-Gly-NH$_2$ | 2923.23 | 2924.25 |
| acAP-PNA 6-1 | Ac-GTAGAT$^{6a\text{-}ac}$CACT-Gly-NH$_2$ | 2965.24 | 2967.09 |
| AP-PNA 6-2 | Ac-GTAGA$^{6a}$TC$^{6a}$ACT-Gly-NH$_2$ | 3022.33 | 3022.94 |
| acAP-PNA 6-2 | Ac-GTAGA$^{6a\text{-}ac}$TC$^{6a\text{-}ac}$ACT-Gly-NH$_2$ | 3106.35 | 3108.15 |
| AP-PNA 6-3 | Ac-G$^{6a}$TAGA$^{6a}$TC$^{6a}$ACT-Gly-NH$_2$ | 3121.44 | 3122.43 |
| AP-PNA 6-4 | Ac-GT$^{6a}$AG$^{6a}$AT$^{6a}$CA$^{6a}$CT-Gly-NH$_2$ | 3220.54 | 3221.32 |
| AP-PNA 6-5 | Ac-GT$^{6a}$AG$^{6a}$AT$^{6a}$CA$^{6a}$CT$^{6a}$-Gly-NH$_2$ | 3319.65 | 3320.70 |
| GP-PNA 6-1 | Ac-GTAGAT$^{6g}$CACT-Gly-NH$_2$ | 2965.25 | 2966.05 |
| GP-PNA 6-2 | Ac-GTAGA$^{6g}$TC$^{6g}$ACT-Gly-NH$_2$ | 3106.38 | 3107.38 |
| GP-PNA 6-3 | Ac-G$^{6g}$TAGA$^{6g}$TC$^{6g}$ACT-Gly-NH$_2$ | 3247.50 | 3248.75 |
| GP-PNA 6-4 | Ac-GT$^{6g}$AG$^{6g}$AT$^{6g}$CA$^{6g}$CT-Gly-NH$_2$ | 3388.63 | 3389.21 |
| GP-PNA 6-5 | Ac-GT$^{6g}$AG$^{6g}$AT$^{6g}$CA$^{6g}$CT$^{6g}$-Gly-NH$_2$ | 3529.75 | 3530.71 | ized
PEPTIDE NUCLEIC ACID MONOMERS AND OLIGOMERS

FIELD OF THE INVENTION

The present invention relates to a peptide nucleic acid, in particular a peptide nucleic acid monomer as well as a corresponding peptide nucleic acid molecule.

BACKGROUND OF THE INVENTION

Peptide nucleic acid (PNA), first reported by Nielsen et al. in 1991, is a synthetic DNA/RNA mimic in which the ribose-phosphodiester backbone is typically replaced by an N-(2-aminoethyl)glycinyl (aeg) amide linkage and the nucleobases are linked to the α-nitrogen of aeg backbone through a methylene carbonyl moiety at approximately the same distance as in natural DNA/RNA (see FIG. 1A; or Nielsen, P. E., et al., *Science* (1991) 254, 1497). This molecular design allows PNA to recognize and hybridize complementary DNA/RNA through Watson-Crick base pairing with high affinity and specificity. Because of its non-peptide non-nucleic acid nature, PNA is not degraded by either nucleases or peptidases and therefore is very stable in vivo. Since PNA is made up of achiral, amino acid-like monomers, it can be easily prepared with well-established peptide synthesis protocols without problems of enantiomeric impurity. Because of these remarkable properties, PNA has the potential to become a leading agent for antigene and antisense applications.

However, like many large oligomeric compounds of similar nature, PNA has poor cell membrane permeability which has severely limited its use in biomedical research (Koppelhus, U., & Nielsen, P. E., *Advanced Drug Delivery Reviews* (2003) 55, 267). Considerable efforts have been devoted to improving PNA cellular uptake during the past decade. Using cell-permeable peptides as PNA-delivery vectors has been a popular approach. When attached to PNA, these peptides have been found effective to deliver the PNA cargo into living cells in various in vitro studies. Alternatively, a more appealing strategy is to design new PNA molecules with built-in cell permeability through incorporating the membrane translocation features of cell-permeable peptides onto the PNA backbone. Many studies have been published describing backbone-modified PNA analogues for this and other purposes. Among these, introducing an amino-acid side chain bearing a positive charge, such as that of lysine, ornithine or arginine at the α- or γ-position of the aeg backbone (FIG. 1B and FIG. 1C), results in improvement in water solubility and cellular uptake. Notably, PNA with either an L-Arg or D-Arg side chain at the aeg α-carbon, i.e., D-Arg$_\alpha$-PNA and L-Arg$_\alpha$-PNA, have been reported to have good cell permeability (Zhou, P., et al., *J. Am. Chem. Soc.* (2003) 125, 6878; Dragulescu-Andrasi, A., et al., *Chem. Comm.* (2005) 244). So far, almost all the modifications have been focused on the aeg backbone carbons which inevitably generate a chiral centre, and the two stereoisomers often exhibit rather different binding behaviours towards complementary DNA or RNA, possibly as a result of differential interstrand or intrastrand steric interactions caused by the two configurations (Sforza, S., et al., *Chirality* (2002) 14, 591). It is therefore of utmost importance to prevent epimerization during monomer synthesis and oligomer assembling to ensure the optical purity of the PNA analogues.

Accordingly, it is an object of the present invention to provide a PNA molecule with properties that overcome at least some of these disadvantages.

SUMMARY OF THE INVENTION

According to a first aspect, the invention provides a peptide nucleic acid monomer. The peptide nucleic acid monomer includes a terminal amino group and a terminal group A. The terminal amino group and the terminal group A are connected by an aliphatic moiety. The main chain of the aliphatic moiety that connects the terminal amino group and the terminal group A is free of groups that are charged under physiological conditions. The terminal group A is one of —COOH, —COOR$^3$, —COX, —COSR$^3$, —CN, —CONH$_2$, —CONHR$^3$ and —CONR$^3$R$^4$. R$^3$ in —COOR$^3$, —COSR$^3$, —CONHR$^3$ and —CONR$^3$R$^4$ as well as R$^4$ in —CONR$^3$R$^4$ are independently selected from the group consisting of H, and an aliphatic, alicyclic, aromatic, arylaliphatic, and arylalicyclic group that includes 0 to about 3 heteroatoms selected from the group N, O, S, Se and Si. X in —COX is a halogen atom. The terminal amino group is substituted by an aliphatic moiety with a main chain of at least two carbon atoms. This main chain further has optionally 0 to about 2 heteroatoms selected from the group N, O, S, Se and Si. This main chain of the aliphatic moiety at the terminal amino group further has a polar head group Z. In particular embodiments this group Z is capable of carrying a charge in aqueous solution.

According to a second aspect, the invention provides a process of forming a peptide nucleic acid monomer. The process includes providing a first bifunctional compound. The first bifunctional compound is an aliphatic compound with a main chain of at least two carbon atoms. This main chain further has optionally 0 to about 2 heteroatoms selected from the group N, O, S, Se and Si. Each end of this main chain has a polar head group. The polar head group on one end is an amino group. The polar head group on the other end is a group Z. The process also includes providing a second bifunctional compound. The second bifunctional compound is also an aliphatic compound. The process includes reacting the amino group of the first bifunctional compound with the second bifunctional compound. Thereby a peptide nucleic acid monomer precursor molecule is formed. The peptide nucleic acid monomer precursor molecule includes a terminal amino group and a terminal group A. The terminal amino group and the terminal group A are connected by an aliphatic moiety. The terminal amino group is substituted by an aliphatic moiety with a main chain of at least two carbon atoms and optionally 0 to about 2 heteroatoms selected from the group N, O, S, Se and Si. This main chain of the aliphatic moiety has optionally 0 to about 2 heteroatoms selected from the group N, O, S, Se and Si. The main chain of the aliphatic moiety further has a polar head group Z. Further, the process includes linking a nucleobase to the peptide nucleic acid monomer precursor molecule. As a result a peptide nucleic acid monomer is formed.

According to a third aspect, the invention provides a peptide nucleic acid molecule. The peptide nucleic acid molecule has an aliphatic backbone that is under physiological conditions at least substantially uncharged. The aliphatic backbone of the peptide nucleic acid molecule includes amide groups. The amino portion of one or more of the amide groups is substituted by an aliphatic moiety with a main chain that has at least two carbon atoms. The alkyl chain also has a polar head group Z.

BRIEF DESCRIPTION OF THE DRAWINGS

The invention will be better understood with reference to the detailed description when considered in conjunction with the non-limiting examples and the accompanying drawings.

FIG. 1 schematically indicates the structures of N-(2-aminoethyl)glycinyl (aeg) PNA and other PNAs. A: aegPNA; B: $C^\alpha$-substituted PNA; C: $C^\gamma$-substituted PNA; D: $N^\gamma$-substituted PNA.

FIG. 2 depicts the overall strategy for the synthesis of the AP-PNA and GP-PNA monomers. Examples of suitable nucleobase-containing compounds are depicted that can be reacted with intermediate compound 1 (see FIG. 6 for further examples).

FIG. 6A: 2-(Adenin-9-yl)propanoic acid, Chemical Abstracts No. 87620-89-1; FIG. 6B: 2-amino-9H-purine-9-acetic acid, CAS No. 933477-63-5; FIG. 6C: 9-carboxymethylhypoxanthine, CAS No. 6298-53-9; FIG. 6D: 2-amino-1,6-dihydro-6-thioxo-9H-purine-9-acetic acid, CAS-No 156006-84-7; FIG. 6E: 2-amino-1,6-dihydro-6-oxo-9H-purine-9-acetic acid, CAS-No 281676-77-5; FIG. 6F: 3,4-dihydro-5-methyl-4-oxo-2-thioxo-1(2H)-pyrimidineacetic acid, CAS-No 84768-19-4; FIG. 6G: 4-amino-a-methyl-2-oxo-1(2H)-pyrimidineacetic acid, CAS No. 102716-43-8; FIG. 6H: 3,4-dihydro-5-methyl-2,4-dioxo-1(2H)-pyrimidineacetamide; CAS No. 195819-71-7. Where desired, a potentially reactive functional group, such as an amino group in FIG. 6A, FIG. 6B, FIG. 6D, FIG. 6E or FIG. 6G, may be protected by a suitable functional group.

FIG. 7 depicts the thermal stabilities (Tm/° C.) of PNA/DNA and PNA/RNA duplexes. The PNA molecules used in FIG. 7A to 7D differed in the length of the alkyl chain bound to the amino portion of the amide groups in the aliphatic backbone of the PNA molecule, as indicated on top of each table. In FIG. 7E selected AP- and GP-PNA molecules (with a 6-, 5-, 4-, 3- or 2-C spacer) were used.

FIG. 8 depicts circular dichroism (CD) spectra of the duplexes between aegPNA, AP-PNA (A) or GP-PNA (B) and the anti-parallel DNA at the concentration of 6 μM.

FIG. 10 is a table depicting the expected and observed masses for examples of AP-PNA and GP-PNA oligomers formed.

DETAILED DESCRIPTION OF THE INVENTION

Figure 3:
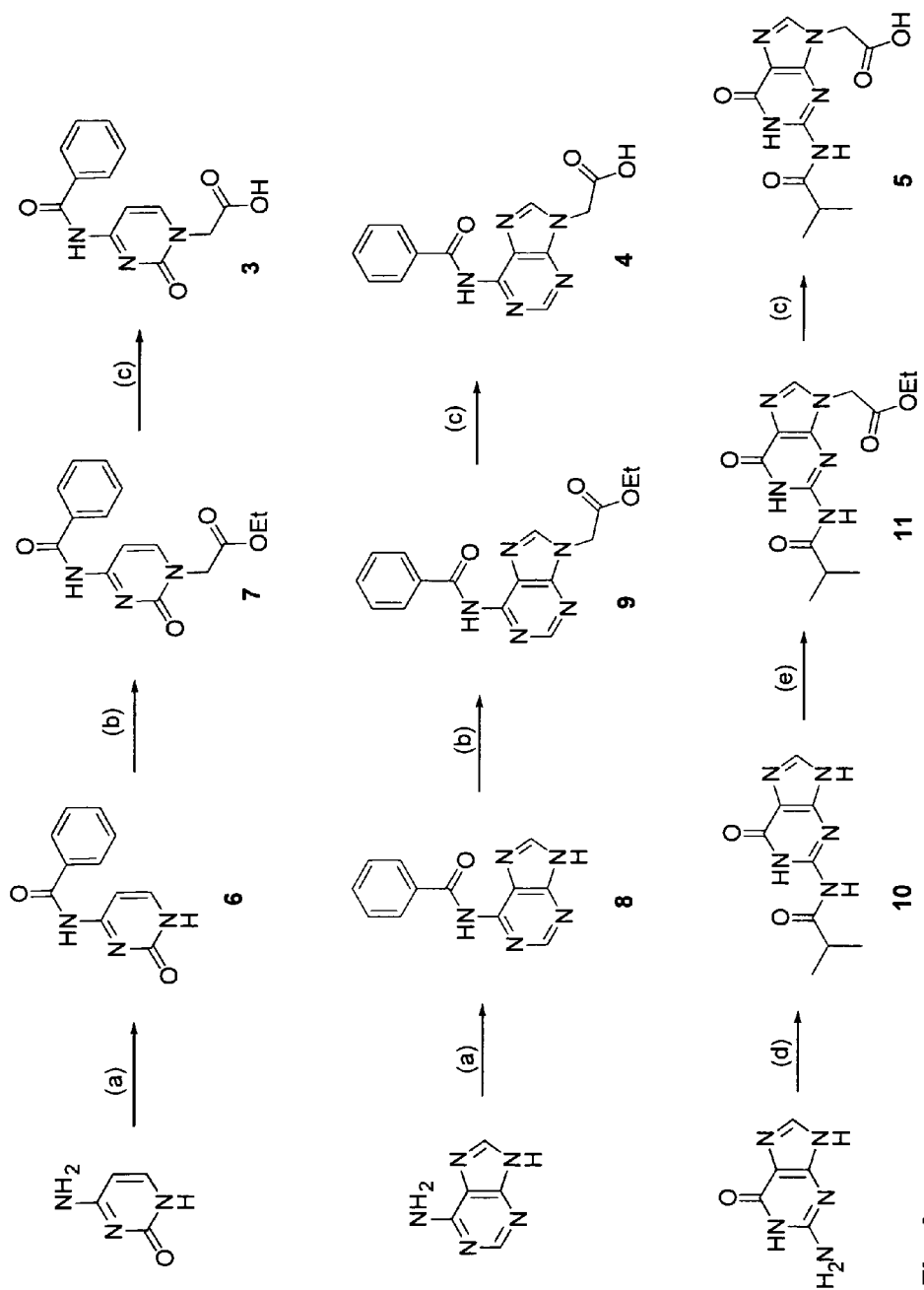
FIG. 3 depicts the synthesis of acyl protected carboxymethyl nucleobases: (a) Benzoyl chloride/pyridine; (b) Ethyl bromoacetate, NaH/DMF; (c) NaOH, $H_2O$; (d) Isobutyryl chloride, DIEA/DMF; (e) Ethyl bromoacetate, $Na_2CO_3$/DMF.

The present invention provides a novel functional PNA monomer and an efficient synthetic process to form this PNA monomer. Using this monomer an oligomeric or polymeric PNA molecule can be formed. A PNA molecule is a nucleic acid molecule in which the backbone is a pseudopeptide rather than a phospho sugar. Accordingly, PNA generally has a charge neutral backbone, in contrast to for example DNA or RNA. Nevertheless, PNA is capable of hybridising at least complementary and substantially complementary nucleic acid strands, just as e.g. DNA or RNA, to which PNA is considered a structural mimic. Since a PNA molecule has a neutral backbone, hybridization with target nucleic acids is furthermore not affected by the interstrand negative charge electrostatic repulsions. The binding of PNA to DNA and RNA targets is accordingly stronger than the binding of DNA to DNA or RNA to RNA. PNA/DNA or PNA/RNA hybrids thus show a very stable duplex formation even at a relatively high temperature, and a very high binding affinity. Additionally, the absence of a repetitively charged backbone also prevents a PNA molecule from binding to proteins that normally have an affinity to polyanions. Hence, the use of PNA avoids a major source of non-specific interactions.

The term "nucleic acid molecule" as used herein refers to any nucleic acid in any possible configuration, such as single stranded, double stranded or a combination thereof. Nucleic acids include for instance DNA molecules, RNA molecules, analogues of the DNA or RNA generated using nucleotide analogues or using nucleic acid chemistry, locked nucleic acid molecules (LNA), PNA molecules (supra) and tecto-RNA molecules (e.g. Liu, B., et al., *J. Am. Chem. Soc.* (2004) 126, 4076-4077). An LNA molecule has a modified RNA backbone with a methylene bridge between C4' and O2', which locks the furanose ring in a N-type configuration, providing the respective molecule with a higher duplex stability and nuclease resistance. Unlike a PNA molecule an LNA molecule has a charged backbone. DNA or RNA may be of genomic or synthetic origin and may be single or double stranded. Such nucleic acid can be e.g. mRNA, cRNA, synthetic RNA, genomic DNA, cDNA synthetic DNA, a copolymer of DNA and RNA, oligonucleotides, etc. A respective nucleic acid may furthermore contain non-natural nucleotide analogues and/or be linked to an affinity tag or a label.

Many nucleotide analogues are known and can be present and/or used (see below) in the molecules and methods of the invention. A nucleotide analogue is a nucleotide containing a modification at for instance the base, sugar, or phosphate moieties. As an illustrative example, a substitution of 2'-OH residues of siRNA with 2'F, 2'O-Me or 2'H residues is known to improve the in vivo stability of the respective RNA. Modifications at the base moiety include natural and synthetic modifications of A, C, G, and T/U, different purine or pyrimidine bases, such as uracil-5-yl, hypoxanthin-9-yl, and 2-aminoadenin-9-yl, as well as non-purine or non-pyrimidine nucleotide bases. Other nucleotide analogues serve as universal bases. Universal bases include 3-nitropyrrole and 5-nitroindole. Universal bases are able to form a base pair with any other base. Base modifications often can be combined with for example a sugar modification, such as for instance 2'-O-methoxyethyl, e.g. to achieve unique properties such as increased duplex stability.

A PNA molecule is a synthetic nucleic acid analogue with a pseudopeptide backbone in which the phosphodiester backbone present in e.g. DNA or RNA is replaced by repetitive units of short aliphatic moieties with an amino end and a carboxylic end, forming an amide bond in the oligomer or polymer. To the short aliphatic moieties of the backbone, nucleobases, usually purine and pyrimidine bases, are attached via a side chain, generally a methyl carbonyl linker. In a PNA molecule according to the invention any desired nucleobase, including purine and pyrimidine bases, may be used. Examples of suitable purine and pyrimidine bases include, but are not limited to, cytosine, 5-methylcytosine, guanine, adenine, thymine, uracil, 5,6-dihydrouracil, hypoxanthine, xanthine, ribothymine, 7-methylguanine or 7-isobutylguanine. A number of further suitable illustrative nucleobases that may also be termed "modified" nucleobases have recently been reviewed by Wojciechowski & Hudson (*Current Topics in Medicinal Chemistry* (2007) 7, 667-679). These include inter alia 4-(1,2,4-triazolyl)thymine, 5-alkynyluracil, 5-iodouracil, thiouracil, 5-(propargyl alcohol)uracil, isocytosine, pseudoisocytosine, 5-(ferrocenylpropargylcarboxamide)uracil, N6-alkyladenine, N7-xanthine, 3-nitropyrrole, 6-thioguanine, phenoxazine, 2-aminopurine or 2,6-diaminopurine.

In a PNA molecule according to the invention, including in a respective PNA monomer, typically the nucleobase of each monomeric unit is bonded to the backbone via a side chain, or a portion of a side chain of the backbone. Thus in some embodiments the nucleobase is bonded to the end of the respective side chain, whereas in other embodiments the nucleobase is bonded to another position along the length of the side chain. This portion of the side chain, or in some embodiments this side chain, is in a PNA molecule according to the invention in typical embodiments of a length of two carbon atoms. In some embodiments the side chain is bonded to the main chain of the PNA monomer, or respectively to the backbone of the PNA molecule, via a heteroatom of the main chain/backbone. The side chain may for example be bonded to the main chain via an amide bond. Thus, the main chain may include a nitrogen heteroatom. This nitrogen atom may by bonded to a carbonyl group of the side chain via a amide bond.

A heteroatom is any atom that differs from carbon. Examples include, but are not limited to N, O, P, S, Si and Se. Where several heteroatoms are present within a moiety of a reactant or product of the process of the invention, they are independently selected.

The short aliphatic moieties in each PNA monomer unit of a PNA molecule, as known in the art, are typically units of N-(2-aminoethyl) glycine (aeg) (supra, see FIG. 1A). On this monomeric unit the PNA monomeric units of a PNA molecule according to the invention may also be based. Hence, monomeric units such as depicted in FIG. 1A, FIG. 1B or FIG. 1C may for instance define the backbone of a PNA molecule according to the invention, as well as the main chain of a corresponding PNA monomer. As further explained below, in the molecules of the invention the amino group of the main chain depicted in these figures is bonded to an additional substituent, as exemplified in FIG. 1D.

An oligomeric PNA molecule is understood to be a molecule that has about 6 to about 15 monomeric units. The PNA backbone maintains the same approximate length per repeating unit as in DNA or RNA and the appended nucleobases project from the backbone to form stable double or triple helical complexes with target nucleic acid molecules. Accordingly, the internucleobase distance in PNA is conserved when compared to DNA or RNA, allowing the binding of PNA to the target nucleic acid sequences with high sequence specificity and affinity.

The backbone of both the PNA molecule and a corresponding PNA monomer may further be achiral if no further substituents are present at the carbon atoms of the mains chain of the monomer(s). The amide bonds in a PNA molecule provide a high biological stability. Furthermore, the non-natural character of PNA—chemically it markedly differs from both DNA/RNA and proteins—renders a PNA molecule highly resistant to protease and nuclease attacks.

A PNA monomer according to the present invention has an aliphatic main chain with a functional group at each of its ends. The term "aliphatic" means, unless otherwise stated, a straight or branched hydrocarbon chain, which may be saturated or mono- or poly-unsaturated and include heteroatoms (see above). An unsaturated aliphatic group contains one or more double and/or triple bonds (alkenyl or alkinyl moieties). The branches of the hydrocarbon chain may include linear chains as well as non-aromatic cyclic elements. The hydrocarbon chain, which may, unless otherwise stated, be of any length, and contain any number of branches. Typically, the hydrocarbon (main) chain includes 1 to about 4, 1 to about 5, 1 to about 6, 1 to about 7, 1 to about 8, 2 to about 4, 2 to about 5, 2 to about 6, 3 to about 4, 3 to about 5, 3 to about 6, 1 to about 10 or 2 to about 10 carbon atoms. Examples of alkenyl radicals are straight-chain or branched hydrocarbon radicals which contain one or more double bonds. Alkenyl radicals normally contain about two to about twenty carbon atoms and one or more, for instance two, double bonds, such as about two to about ten carbon atoms, and one double bond. Alkynyl radicals normally contain about two to about twenty carbon atoms and one or more, for example two, triple bonds, such as two to ten carbon atoms, and one triple bond. Examples of alkynyl radicals are straight-chain or branched hydrocarbon radicals which contain one or more triple bonds. Examples of alkyl groups are methyl, ethyl, propyl, butyl, pentyl, hexyl, heptyl, octyl, nonyl, decyl, the n isomers of these radicals, isopropyl, isobutyl, isopentyl, sec.-butyl, tert.-butyl, neopentyl and 3,3-dimethylbutyl. Both the main chain as well as the branches may furthermore contain heteroatoms as for instance N, O, S, Se or Si or carbon atoms may be replaced by these heteroatoms. In some embodiments the aliphatic main chain of the peptide nucleic acid monomer includes from 0 to about 4, such as from 0 to about 3 or from 1 to about 3 such heteroatoms. In some embodiments the nucleobase is linked to a heteroatom of main chain of the PNA monomer via a linking moiety. As explained above, the corresponding heteroatom may be nitrogen and the linking moiety may be bonded to the nitrogen atom via an amide bond.

The term "alicyclic" may also be referred to as "cycloaliphatic" and means, unless stated otherwise, a non-aromatic cyclic moiety (e.g. hydrocarbon moiety), which may be saturated or mono- or poly-unsaturated. The cyclic hydrocarbon moiety may also include fused cyclic ring systems such as decalin and may also be substituted with non-aromatic cyclic as well as chain elements. The main chain of the cyclic hydrocarbon moiety may, unless otherwise stated, be of any length and contain any number of non-aromatic cyclic and chain elements. Typically, the hydrocarbon (main) chain includes 3, 4, 5, 6, 7 or 8 main chain atoms in one cycle. Examples of such moieties include, but are not limited to, cyclopentyl, cyclohexyl, cycloheptyl, or cyclooctyl. Both the cyclic hydrocarbon moiety and, if present, any cyclic and chain substituents may furthermore contain heteroatoms, as for instance N, O, S, Se or Si, or a carbon atom may be replaced by these heteroatoms. The term "alicyclic" also includes cycloalkenyl moieties that are unsaturated cyclic hydrocarbons, which generally contain about three to about eight ring carbon atoms, for example five or six ring carbon atoms. Cycloalkenyl radicals typically have a double bond in the respective ring system. Cycloalkenyl radicals may in turn be substituted.

As already indicated above, both the terms "aliphatic" and "alicyclic", as used herein, are meant to include both substituted and unsubstituted forms of the respective moiety. Substituents may be any functional group such as —COOH (carboxy), —OH (hydroxy), —SH (thiol-), a dithiane-, —SeH (seleno-), —CHO (aldehyde), —CO-(carbonyl), —OSO-(sulfonyl), sulfo-, sulfido-, —O-(oxo), sulfate (—OSO$_3$H), —NH$_2$ (amino), —NO (nitro), —NS, —NSe, a halogen such as —Br (bromo), —Cl (chloro) or —F (fluoro), an amino-, an imino-, an amido-, an imido-, an azido-, a diazo-, a cyano-, an isocyano-, a thiocyano-, a nitro-, a nitroso-, asulfonyl- (e.g. a trifluoromethyl sulfonyl-, p-toluenesulfonyl-, bromobenzenesulfonyl-, nitrobenzenesulfonyl-, or a methane-sulfonyl), silyl-, silano- or a siloxy-group.

The aliphatic moiety of the peptide nucleic acid monomer that connects the terminal amino group and the terminal group A may include one or more branches. A respective branch may be bonded back to the aliphatic moiety of the peptide nucleic acid monomer and thereby define a cyclic moiety. The main chain of the aliphatic moiety of the peptide nucleic acid monomer is devoid of groups that have a charge under physiological conditions, i.e. under conditions that resemble the physiological environment in a host or a cell, in particular in terms of the pH value (see also below). Accordingly, in an aqueous solution with a pH value of around ~6.0 to ~8.5, such as around ~6.8 to ~7.5, the aliphatic moiety of the peptide nucleic acid monomer is at least substantially uncharged. A peptide nucleic acid molecule formed from corresponding monomers therefore has an at least substantially uncharged backbone (see also above).

One of the functional groups at the ends of the aliphatic main chain of the PNA monomer according to the invention is an amino group. This terminal amino group is generally one of a secondary and a tertiary amino group. One substituent that the amino group is carrying is an aliphatic moiety. This aliphatic moiety may be straight or branched and optionally include 0 to about 3 heteroatoms, such as 0 to about 2 heteroatoms, including one heteroatom. The main chain of the aliphatic moiety has at least two carbon atoms. The main chain may for instance have a length of about 2 to about 12 carbon atoms, such as 2 to about 10 carbon atoms, about 2 to about 8 carbon atoms, about 2 to about 7 carbon atoms, about 2 to about 6 carbon atoms, about 2 to about 5 carbon atoms, about 2 to about 4 carbon atoms, about 3 to about 10 carbon atoms, about 3 to about 8 carbon atoms, about 3 to about 7 carbon atoms, about 3 to about 6 carbon atoms, about 3 to about 5 carbon atoms, about 4 to about 10 carbon atoms, about 4 to about 8 carbon atoms or about 4 to about 6 carbon atoms, e.g. 2, 3, 4, 5, 6 or 7 carbon atoms.

The main chain of the aliphatic moiety that is bonded to the nitrogen of the amino group of aliphatic main chain of the PNA monomer further has a polar head group Z. The group Z may be any polar group such as a hydroxyl group (—OH), a thio group (—SH), a seleno group (—SeH), a phosphonate group

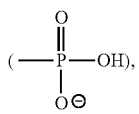

a sulfonate group

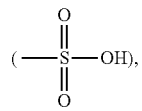

an ester group or an amide group, e.g. of the formula —CONHR$^3$ or —CONR$^3$R$^4$, where R$^3$ and R$^4$ are independently selected H or one of an aliphatic, alicyclic, aromatic, arylaliphatic, and arylalicyclic group that includes 0 to about 3 heteroatoms selected from the group N, O, S, Se and Si (see also above). The group Z may also include a carbonyl group. It may for example be an aldehyde or a carboxyl group. In some embodiments this group Z is capable of carrying a charge in aqueous solution, such as a positive or a negative charge. The group Z may for example be capable of carrying a charge in aqueous solution under conditions where the peptide nucleic acid monomer is at least substantially stable for a period of time, in which the peptide nucleic acid monomer can undergo a desired chemical or biochemical reaction, including a detection or a binding reaction. When the PNA monomer is included in a PNA molecule, the group Z may be capable of carrying a charge in aqueous solution under conditions where the peptide nucleic acid monomer is at least substantially stable for a period of time, in which the peptide nucleic acid molecule can undergo a desired chemical or biochemical reaction, including a detection or a binding reaction, e.g. a hybridization. The group Z may be capable of carrying a charge in aqueous solution in a pH range from about 5 to about 11, such as a pH range from about 5.5 to about 10, a pH range from about 5.5 to about 9 or from about 6 to about 8. In some embodiments the group Z is capable of carrying a charge in aqueous solution under physiological condition, i.e. under conditions that resemble the physiological environment, for instance in a cell or in a host organism. In particular physiological conditions refer to a pH value that approximates a pH value of about 7. Three illustrative examples of a respective polar head group Z are an amino group, a guanidine group and an imidazole group.

In this regard, the term "guanidine group" refers to a moiety of one of the following formulas:

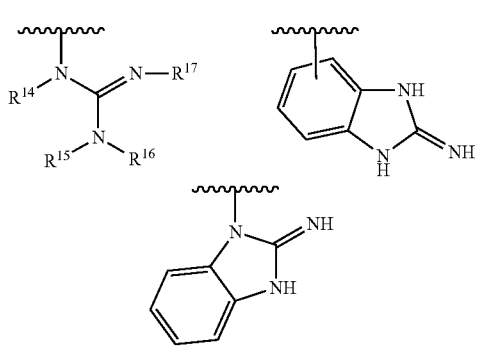

R$^{14}$ to R$^{17}$ in the first of the forgoing formulas may, independently selected, be H, a silyl-group, an aliphatic, alicyclic, aromatic, arylaliphatic, or arylalicyclic group.

The terms "aromatic" and "aryl" mean, unless otherwise stated, a planar cyclic hydrocarbon moiety of conjugated double bonds, which may be a single ring or include multiple fused or covalently linked rings, for example, 2, 3 or 4 fused rings. The term aromatic also includes alkylaryl. Typically, the hydrocarbon (main) chain includes 5, 6, 7 or 8 main chain atoms in one cycle. Examples of such moieties include, but are not limited to, cylcopentadienyl, phenyl, naphthalenyl-, [10]annulenyl-(1,3,5,7,9-cyclodecapentaenyl-), [12]annulenyl-, [8]annulenyl-, phenalene (perinaphthene), 1,9-dihydropyrene, chrysene (1,2-benzophenanthrene). An example of an alkylaryl moiety is benzyl. The main chain of the cyclic hydrocarbon moiety may, unless otherwise stated, be of any length and contain any number of heteroatoms, as for instance N, O and S. Examples of such heteroaromatic moeities (which are known to the person skilled in the art) include, but are not limited to, furanyl-, thiophenyl-, naphthyl-, naphthofuranyl-, anthrathiophenyl-, pyridinyl-, pyrrolyl-, quinolinyl, naphthoquinolinyl-, quinoxalinyl-, indolyl-, benzindolyl-, imidazolyl-, oxazolyl-, oxoninyl-, oxepinyl-, benzoxepinyl-, azepinyl-, thiepinyl-, selenepinyl-, thioninyl-, azecinyl-(azacyclodecapentaenyl-), diazecinyl-, azacyclododeca-1,3,5,7, 9,11-hexaene-5,9-diyl-, azozinyl-, diazocinyl-, benzazocinyl-, azecinyl-, azaundecinyl-, thia-[11]annulenyl-, oxacyclotrideca-2,4,6,8,10,12-hexaenyl- or triazaanthracenyl-moieties.

By the term "arylaliphatic" is meant a hydrocarbon moiety, in which one or more aromatic moieties are substituted with one or more aliphatic groups. Thus the term "arylaliphatic" also includes hydrocarbon moieties, in which two or more aryl groups are connected via one or more aliphatic chain or chains of any length, for instance a methylene group. Typically, the hydrocarbon (main) chain includes 5, 6, 7 or 8 main chain atoms in each ring of the aromatic moiety. Examples of arylaliphatic moieties include, but are not limited, to 1-ethyl-naphthalene, 1,1'-methylenebis-benzene, 9-isopropylanthracene, 1,2,3-trimethyl-benzene, 4-phenyl-2-buten-1-ol, 7-chloro-3-(1-methylethyl)-quinoline, 3-heptyl-furan, 6-[2-(2,5-diethylphenyl)ethyl]-4-ethyl-quinazoline or, 7,8-dibutyl-5,6-diethyl-isoquinoline.

Similar to the terms "aliphatic" and "alicyclic" (supra), the terms "aromatic", "aryl" and "arylaliphatic" as used herein are meant to include both substituted and unsubstituted forms of the respective moiety. Substituents may be or include any functional group, as exemplified above.

As noted above, in some embodiments the terminal amino group of the PNA monomer is a tertiary amino group. Accordingly, in such embodiments a further substituents in addition to the alkyl chain of at least two carbon atoms is bonded to the amino group. Generally this further substituent is of a nature that allows its removal from the amino group under conditions where the remaining PNA monomer remains at least substantially intact. Upon removal of this substituent a protecting group shielding a functional group present in the PNA monomer may for instance be removed while the residual PNA monomer remains unchanged. Accordingly, this additional substituent is typically an amino protecting group. Examples of a suitable protecting group include, but are not limited to, a carbamate group, a methylaryl group (such as phtaloyl- or tetrachlorophtaloyl-), an acetamido group, a trifluoroacetamido group, an arylsulfonyl group (e.g., p-toluolsulfonyl-), an o-nitrophenylsulfenyl group, a trifluoroacetyl group, a trityl group, an ally! group, a 9-phenylfluorenyl group, a dithiasuccinyl group, a triazinanone group, an N-bis(methylthio)methylene group or an N-diphenylmethylene group. Examples of a carbamate group include, but are not limited to, a methoxycarbonyl-, an ethoxycarbonyl-, a benzylcarbonyl-, a benzyloxycarbonyl-, a nitrobenzyloxycarbonyl-, a benzhydryloxycarbonyl-, an allyloxycarbonyl-, a tert-butoxycarbonyl-, a 9-fluorenylmethoxycarbonyl-, a 2-(trimethylsilyl)ethoxycarbonyl-, a 2,2,2-trichloroethoxycarbonyl- and a 2-(4-trifluoromethylphenylsulfonyl)ethoxycarbonyl group. 9-Fluorenylmethoxycarbonyl- and benzhydryloxycarbonyl groups are examples of commonly used amino protecting groups in the synthesis of conventional PNA molecules (see e.g. Shakeel, S., et al., *J. Chem. Technol. Biotechnol.* (2006) 81, 892-899).

The functional group at the other end of the aliphatic main chain of a PNA monomer according to the invention is a functional group that is or can be converted to a carboxylic group. This group, also termed the terminal group A, may thus be a carboxylic group, —COOH, itself. The group A may for instance also be —COOR$^3$, —COX, —COSR$^3$, —CN, —CONH$_2$, —CONHR$^3$ or —CONR$^3$R$^4$. R$^3$ in the groups —COOR$^3$, —COSR$^3$, —CONHR$^3$ and —CONR$^3$R$^4$ may be H, or an aliphatic, alicyclic, aromatic, arylaliphatic or arylalicyclic group that includes 0 to about 3 heteroatoms, i.e. atoms that differ from carbon. Examples of suitable heteroatoms include, but are not limited to, N, O, S, Se and Si. Likewise, and in —CONR$^3$R$^4$R$^4$, are independently selected from the group consisting of H, and an aliphatic, alicyclic, aromatic, arylaliphatic, and arylalicyclic group comprising 0 to about 3 heteroatoms selected from the group N, O, S, Se and Si. X in —COX is a halogen atom such as F, Cl, Br or I.

In some embodiments the peptide nucleic acid monomer according to the invention is of the general structural formula (Id):

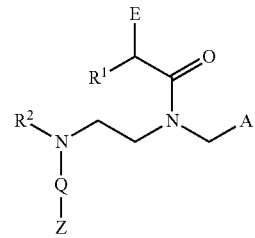

In this formula Q is an aliphatic bridge that may be linear or branched. It has a main chain of a length from about 2 to about 12 carbon atoms, such as from about 3 to about 10 carbon atoms, from about 3 to about 8 carbon atoms, about 4 to about 8 carbon atoms, or about 3 to about 6 carbon atoms. The main chain of the aliphatic bridge Q optionally includes 0 to about 2 heteroatoms such as N, O, S, Se and Si. The aliphatic bridge Q may for instance include an amide bond such as in the following example shown in FIG. 7D:

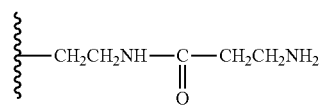

In the above formula (Id) R$^2$ is a silyl-group, an aliphatic, alicyclic, aromatic, arylaliphatic, or arylalicyclic group. In some embodiments R$^2$, is a removable amino-protecting group (see above for examples). Z is the polar head group, which may in some embodiments be capable of carrying a charge in aqueous solution, e.g. an amino group, an amido group, a carboxyl group, an ester group, a hydroxyl group, a thio group, a seleno group, a phosphonate group, a sulfonate group, a guanidine or an imidazole group, R$^1$ may be H, a silyl-group or a methyl group. E is the nucleobase and E may be an individually selected nucleobase. The terminal group A has already been defined above.

In the above formula (Id) the carbon atom, to which the $R^1$ and the nucleobase are bonded, defines a chiral center if $R^1$ is different from H. The bond between this carbon atom and $R^1$ may have any configuration, such that any enantiomer of the PNA monomer as well as any stereoisomer or a mixture of such stereoisomers of a PNA molecule may be selected.

In embodiments where $R^1$ is H, the peptide nucleic acid monomer can also be represented by the general structural formula (I):

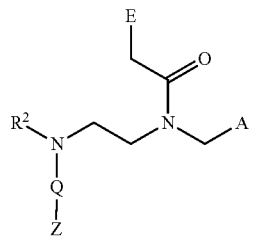

In some embodiments the peptide nucleic acid monomer according to the invention is of the general structural formula (Ic):

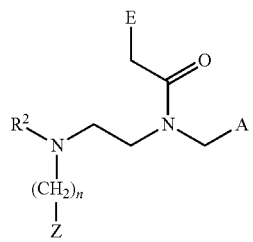

In this formula n is an integer from about 2 to about 15, such as about 2 to about 9, about 2 to about 9, about 2 to about 8, about 2 to about 7, about 2 to about 6, about 3 to about 9, about 3 to about 8, about 3 to about 7, about 3 to about 6, about 4 to about 7, about 4 to about 8 or about 4 to about 6, such as e.g. 2, 3, 4, 5, 6, 7, 8, 9 or 10. E and Z are as defined above. In some embodiments the peptide nucleic acid monomer according to the invention is of one of the general structural formulas (Ia) and (Ib):

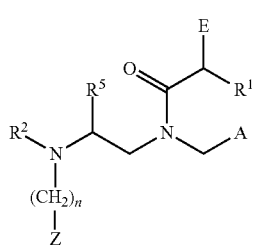

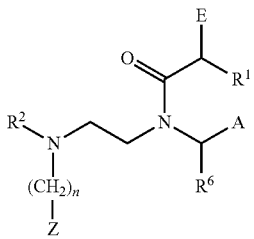

In these formulas n, E, Z, $R^1$ and $R^2$ are as defined above. $R^5$ in formula (Ia) and $R^6$ in formula (Ib) are independently selected from the group consisting of a silyl-group, an aliphatic, alicyclic, aromatic, arylaliphatic, and arylalicyclic group that includes 0 to about 4 heteroatoms selected from the group N, O, S, Se and S. Accordingly, $R^5$ and $R^6$ may also have one or more functional groups. It is noted that the carbon atoms, to which the moieties $R^5$ and $R^6$ are bonded, defines a chiral center. The respective bond may have any configuration, such that any enantiomer or diastereomer of the PNA monomer as well as any stereoisomer or a mixture of such stereoisomers of a PNA molecule may be selected. While substituents $R^5$ and $R^6$ may be selected as desired, no respective substituent is required in order to e.g. improve the cell permeability of the PNA monomers and PNA molecules according to the invention, e.g. by providing a polar group.

The process of forming a PNA monomer according to the invention may be started from any desired structural portion of the PNA monomer. Thus, for example, the main chain may be provided and to its amino group the side chain carrying the polar head group Z may be attached, as well as the nucleobase together with a suitable linking moiety. In some embodiments the synthesis starts from the side chain that is, in the final PNA monomer, bound to the amino group of the main chain of the same and that carries the polar head group Z. In some embodiments the entire aliphatic moiety that is carrying the group Z in the PNA monomer will be provided in the form of a reactant. As noted above, this moiety may include heteroatoms and side chains or branches. In one such embodiment the main chain of the final PNA monomer is formed stepwise. In a first step a precursor of the main chain is provided, in which the atom, e.g. the heteroatom, or a functional group that can be converted to the respective (hetero)atom, is included. In a second step the main chain is completed and the terminal group A is provided or formed, or a functional group that can be converted to the terminal group A.

Accordingly, in some embodiments the process of forming a PNA monomer includes providing a first bifunctional compound, which defines the aliphatic moiety that carries the group Z and that may in some embodiments be termed a side chain. Accordingly, the first bifunctional compound is an aliphatic compound that may include heteroatoms such as N, O, S, Se and Si (see above). The first bifunctional compound may for example be a bifunctional silaalkane, a bifunctional silaalkene, a bifunctional chalcogeno alkane such as a thio-, a seleno- or a telluro-alkane, a bifunctional chalcogeno alkene or a bifunctional aza-, or oxa-alkane. The main chain of this first bifunctional compound has at least two carbon atoms. Besides the group Z, being a first polar head group, the first bifunctional compound has a second polar head group. The second polar head group is an amino group. The amino group is generally a primary or a secondary amino group. Where the amino group is a secondary amino group, it may for instance be bonded to the moiety $R^2$ (supra), which may in some embodiments be a removable amino-protecting group. The two polar head groups are bonded to the two ends of an alkyl chain of at least two carbon atoms, such as about 2 to about 8, about 2 to about 7 or about 3 to about 7 carbon atoms (see also above).

In such embodiments of the process of forming the PNA monomer a second bifunctional compound may be provided. The second bifunctional compound is also an aliphatic compound. The two functional groups of the second bifunctional compound may for instance be two headgroups bonded to the two ends of the main chain of the respective aliphatic compound. One of the two functional groups is generally capable of reacting with the amino group of the first bifunctional compound. The other functional group may be any functional group. This functional group is in some embodiments of a nature that it can be used for a chemical reaction, e.g. a conversion. Such a conversion may lead to the formation of the heteroatom of a main chain of the PNA monomer, to which the nucleobase is to be coupled via a linking moiety (supra). Such a conversion may also result in the formation of the terminal group A of the PNA monomer. In some embodiments the main chain of the second bifunctional compound is provided by providing the second bifunctional compound (see also above). This main chain may include a heteroatom, to which the nucleobase can be coupled via a linking moiety.

The second bifunctional compound is reacted with the amino group of the first bifunctional compound. In embodiments where the amino group of the first bifunctional compound is a primary amino group, it is accordingly converted into a secondary amino group. In embodiments where the amino group of the first bifunctional compound is a secondary amino group, it is generally converted into a tertiary amino group. In some embodiments the secondary amino group of the first bifunctional compound may have been bonded to a labile protective group, which may be cleaved or removed during the reaction with the second bifunctional compound. In such embodiments the respective secondary amino group of the first bifunctional compound may be converted to another secondary amino group. In some embodiments the amino group of the first bifunctional compound is a primary amino group and converted into a secondary amino group, and consecutively or simultaneously converted into a tertiary amino group. As an example, a secondary amino group may be formed, which is the protected with a suitable protecting group.

As a result of the reaction between the first and the second bifunctional compound, a peptide nucleic acid monomer precursor molecule may be formed, which may include a terminal amino group and a terminal group A. The peptide nucleic acid monomer precursor molecule may for example be of the general structural formula (VI):

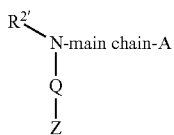

In this formula Q, A and Z are as defined above. $R^{2'}$ may represent $R^2$ or a moiety that can be converted to $R^2$ without at least substantially affecting or derogating the residual structure and functional groups of the peptide nucleic acid precursor molecule. As an illustrative example, upon converting $R^{2'}$ to $R^2$, any protecting group present in the molecule, such as an ester, an amide or an ether may be cleaved to the free corresponding functional group, e.g. a carboxylic acid, amine or hydroxyl group—whereas any non-protected functional groups or other moieties within the molecule remain unchanged. The main chain of the aliphatic moiety that connects the terminal amino group and the terminal group A of the peptide nucleic acid monomer precursor molecule may optionally include 0-3 heteroatoms such as N, O, S, Se and Si.

In some embodiments the peptide nucleic acid monomer precursor molecule may be of the general structural formula (VIa)

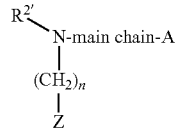

In this formula n, A, Z and $R^{2'}$ are as defined above.

During the process of forming a PNA monomer according to the invention the nucleobase is further bonded to the peptide nucleic acid monomer precursor molecule. Thereby the peptide nucleic acid monomer may be formed. As already explained above, in some embodiments the main chain of the PNA monomer precursor molecule has a heteroatom to which, or to the position of which, the nucleobase is being linked. In such embodiments the heteroatom may for instance be N or Si. A linking moiety may be bonded to the position of the heteroatom that carries the nucleobase, thereby forming a side chain of the peptide nucleic acid monomer. In some embodiments the portion of the linking moiety that is turned into the portion of the side chain that connects the nucleobase to the main chain has a length of two carbon atoms. As already indicated above, the side chain that connects the nucleobase to the main chain may be connected to the main chain via an amide bond. Accordingly, such an amide bond may be formed during the process of linking the side chain to a heteroatom of the main chain. The heteroatom is in such embodiments generally a nitrogen atom.

In embodiments where the main chain of the final PNA monomer is formed stepwise, an intermediate compound may be formed. In some embodiments such an intermediate compound is formed upon reacting the amino group of the first bifunctional compound with a functional group of a second bifunctional compound. This second bifunctional compound is also an aliphatic compound. The formed intermediate compound may include a terminal amino group and a terminal functional group G. These two groups may be connected by an aliphatic moiety. Furthermore, the terminal amino group is substituted by an aliphatic moiety with a main chain of at least two carbon atoms and optionally 0 to about 2 heteroatoms (supra). The latter alkyl main chain of at least two carbon atoms has a polar head group Z that may in some embodiments be capable of carrying a charge in aqueous solution. In such embodiments the terminal functional group G of the intermediate compound may define the position of a heteroatom in the final PNA monomer to which the linking moiety carrying the nucleobase is connected.

The functional group G may also be converted into another moiety, whereby a position may be introduced, which corresponds to the position of the respective heteroatom in the final PNA monomer. The functional group G may be reacted with a functional group of a third bifunctional compound. The third bifunctional compound is also an aliphatic compound. As a result the peptide nucleic acid monomer precursor molecule may be formed. Thereby the terminal functional group G of the intermediate compound may be converted to a heteroatom of the peptide nucleic acid monomer precursor molecule.

As explained in detail above, in some embodiments the peptide nucleic acid monomer is defined by the general structural formula (I) (supra). In the process of forming such a peptide nucleic acid monomer a peptide nucleic acid precursor molecule of the general structural formula (III) may be employed:

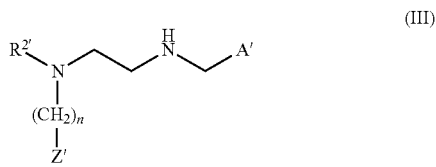
(III)

As explained above, $R^{2'}$ may be identical to $R^2$, or it may for instance be a shielded form of $R^2$, with $R^{2'}$ being convertible to $R^2$. Likewise, in the above formula (III) A' may also be identical to A or it may be a shielded form of A, with A' being convertible to A. Also Z' may be identical to Z, or it may for instance be a shielded form of Z, with Z' being convertible to Z. n is an integer as defined above.

The peptide nucleic acid precursor molecule may be reacted with a compound of general formula (IV) to form the peptide nucleic acid monomer of general structural formula (I) (see above).

(IV)

In the above formula (IV) Y may be —COOH, —COOR$^3$, —COX, —COSR$^3$, —CN, —CONH$_2$, —CONHR$^3$ or —CONR$^3$R$^4$. In —COOR$^3$, —COSR$^3$, CONHR$^3$ and —CONR$^3$R$^4$ the moiety R$^3$, as well as in —CONR$^3$R$^4$ the moiety R$^4$, are independently selected H, or an aliphatic, alicyclic, aromatic, and arylalicyclic group, which may include 0 to about 3 heteroatoms such as N, O, S, Se and Si. X in —COX is a halogen atom, e.g. F, Cl, Br or I. R$^1$ may be H, a silyl-group or a methyl group. E may be an individually selected nucleobase In some embodiments the peptide nucleic acid precursor molecule of the general structural formula (III) may be obtained from a compound of general formula (VII):

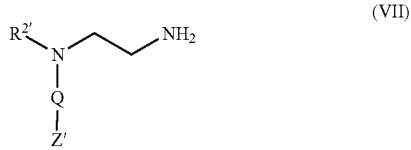
(VII)

The primary amino group of the compound of general formula (VII) may for instance be reacted with a compound of formula L-CH$_2$-A', in which L is a suitable leaving group for a reaction with an amino group. Thereby the compound of general formula (III) may be obtained.

In some embodiments the compound of general formula (VII) may be a compound of general formula (VIIa):

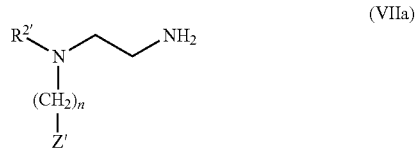
(VIIa)

In some embodiments the peptide nucleic acid precursor molecule of the general structural formula (III) may be obtained from a compound of general formula (VIII):

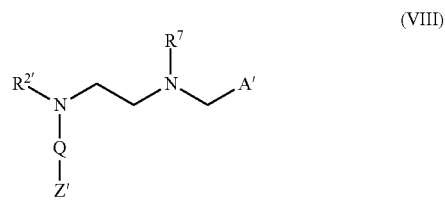
(VIII)

In this formula (VIII) the moiety R$^7$ may be a suitable protective group that can conveniently be removed from the molecule (see above for examples). R$^{2'}$, A', Z' and n are as defined above. In some embodiments the compound of general formula (VIII) may be a compound of general formula (VIIIa):

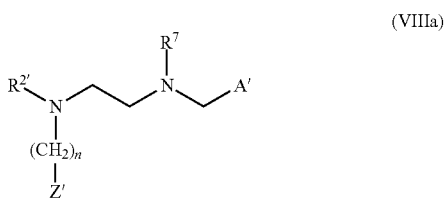
(VIIIa)

In some embodiments the peptide nucleic acid precursor molecule of the general structural formula (III) may be obtained from an intermediate compound of general formula (V):

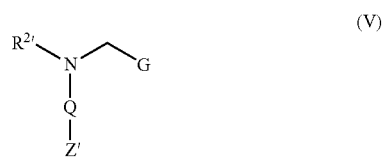
(V)

In this formula (V) R$^{2'}$, Z' and n are as defined above. The moiety G may be one of a formyl group, a halogenomethylene group, an acetal, a thioacetal and a selenoacetal. In some embodiments the compound of general formula (V) may be a compound of general formula (Va):

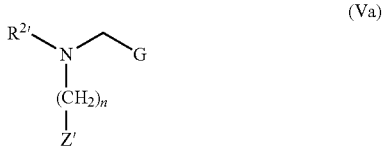
(Va)

By reacting the intermediate compound of general formula (V) with glycine or an ester of glycine a nucleic acid precursor molecule of the general structural formula (III) may be obtained.

A PNA molecule according to the invention has an aliphatic backbone that is under physiological conditions at least substantially uncharged. The aliphatic backbone includes amide groups, which typically connect the monomeric subunits of the PNA molecule. An amino portion of these amide bonds may be included in one monomeric subunit whereas the carbonyl portion may be included in another monomeric subunit. Generally the one or more amide groups of the aliphatic backbone of the PNA molecule are connected by aliphatic moieties. These aliphatic moieties are accordingly typically included in the backbone of the PNA molecule. These aliphatic moieties may include 0-3 heteroatoms such as N, O, S, Se and Si.

In a PNA molecule according to the invention the amino portion of one or more of the amide groups is substituted by an alkyl side chain of at least two carbon atoms. This alkyl chain has a polar head group Z, which may in some embodiments be capable of carrying a charge, e.g. a positive charge or a negative charge in aqueous solution. In some embodiments the polar head group Z is capable of carrying a charge under physiological conditions (supra). The polar head group Z may for instance be an amino group, a guanidine group or an imidazole group.

A PNA molecule according to the invention may be obtainable by a process that includes reacting a plurality of peptide nucleic acid monomers. Such a process may also include immobilizing the growing PNA molecule on a solid support. Generally any standard method, as well known to those skilled in the art may, in the formation of PNA molecules may be employed. Any step or combination of steps of the method may also be carried out in an automated manner.

A PNA molecule according to the invention may have monomeric units that can be represented by the general structural formula (II):

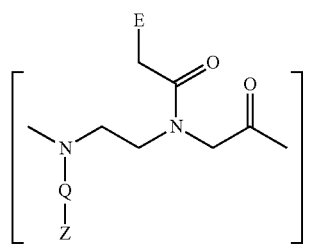
(II)

In general formula (II) Q is an aliphatic bridge that has a main chain of a length from about 2 to about 12 carbon atoms. Additionally it may optionally include 0 to about 2 heteroatoms such as N, O, S, Se and Si. E is an individually selected nucleobase. Z is an individually selected polar head group, which may in some embodiments be capable of carrying a charge in aqueous solution.

In some embodiments the compound of general formula (V) may be a compound of general formula (IIa):

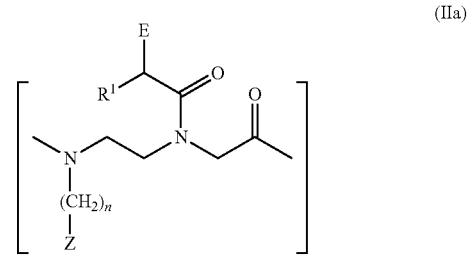
(IIa)

In general formula (IIa) n is an individually selected integer from 2 to about 9, such as about 2 to about 8, about 2 to about 7, about 2 to about 6, about 3 to about 9, about 3 to about 8, about 3 to about 7, about 3 to about 6, about 4 to about 7 or about 4 to about 6, such as e.g. 2, 3, 4, 5, 6, 7 or 8.

As an illustrative example a PNA molecule according to the invention may include a substructure that can be represented as follows:

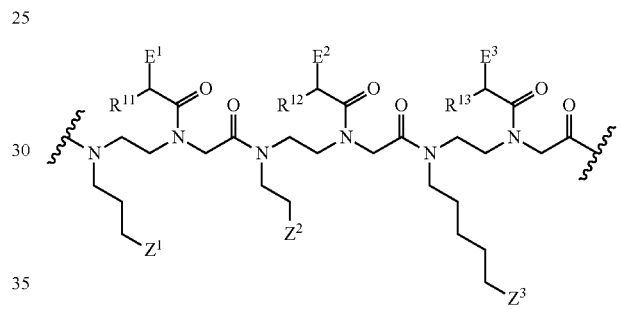

In the above exemplary substructure moieties $E^1$ to $E^3$ are individually selected nucleobases. $Z^1$ to $Z^3$ are individually selected polar head groups. These polar head groups may be capable of carrying a charge in aqueous solution. $R^{11}$ to $R^{13}$ are individually selected moieties that may be H, a silyl-group or a methyl group.

PNA molecules are usually poorly soluble in aqueous solutions. Those skilled in the art will therefore appreciate that the presence of the polar head group Z generally results in a substantial improvement of solubility of a PNA molecule according to the invention when compared to conventional PNA molecules.

PNA molecules are known to be capable of hybridizing to both complementary DNA and RNA targets in a sequence-specific manner to form a PNA/DNA and a PNA/RNA duplex structure according to the Watson-Crick hydrogen binding scheme. This also applies to the PNA molecules of the invention. In contrast to DNA, PNA can bind in either parallel or antiparallel fashion. However, the antiparallel binding is slightly favoured over the parallel one and has a higher thermal stability.

As PNA in general, PNA molecules according to the invention may be used in various applications. They may for instance serve as a molecular tool in molecular biology and biotechnology or they may be used for therapeutic purposes, as well as in the development of gene-targeted drugs, by inhibiting gene transcription, i.e. typically antisense applications. They may further be employed to inhibit the elongation of nucleic acid primers, in particular DNA primers, by a respective polymerase in a variety of applications. As another example, they may be employed for diagnostic purposes or in the development of biosensors. Further, they may be employed as adapters to link peptides, pharmaceutical compounds or molecular tracers to plasmid vectors.

In order that the invention may be readily understood and put into practical effect, particular embodiments will now be described by way of the following non-limiting examples.

EXAMPLES

Material and Methods

All solvents used were of analytical grade. Pyridine, DMF and DCM were dried using anhydrous $Na_2SO_4$ for one or two days, distilled and stored over molecular sieves prior to usage. NaH was washed with dry hexane and dried in vacuo prior to use. Guanine was purified by dissolving it in 0.5 M NaOH, and subsequently adjusting the pH of the solution to pH 10 using 1M HCl; The white precipitate formed was collected, dried and ground to a fine powder prior to usage. All other chemicals supplied by Aldrich, Merck and Lancaster were used without further purification.

Flash chromatography was carried out using commercial silica columns (Redisep) on a CombiFlash system, and manual preparative column chromatography was carried out using silica gel 60 (Lancaster, 0.040-0.063 mm). Analytical HPLC was performed on a DIONEX system equipped with a PDA-100 photodiode array detector and a C18 reversed-phase column (Agilent, 4.6×150 mm). Semi-preparative HPLC was carried out on a SHIMADZU system with a C18 semi-preparative column. The analytes were eluted using a gradient mixture of two solvents: Solvent A was distilled deionized water containing 0.045% TFA and solvent B was 90% ACN in distilled deionized water containing 0.04% TFA. The mobile phase flow rate was 1 mL/min for analytical and 2.5 mL/min for semi-preparative HPLC respectively, and the separation temperature was 23° C.

The $^1H$ and $^{13}C$ NMR spectra were recorded on a Bruker DRX-400 (400 MHz) NMR spectrophotometer. ESI/APCI mass spectra were recorded using a bench-top ion trap mass spectrometer (FINNIGAN LCQ Deca XP MAX) equipped with standard ESI/APCI sources. MALDI-TOF mass spectra of PNA oligomers were recorded on a 4800 MALDI TOF/TOF Analyzer operating in MS reflector positive ion mode and using α-cyno-4-hydroxycinnamic acid as the matrix.

Thermal denaturation studies (Tm) were run on a Cary 300 Bio UV-Visible spectrophotometer. DNA oligos were purchased from SIGMA PROLIGO. The oligomers were hybridized in a buffer solution containing 100 mM NaCl, 10 mM sodium phosphate and 0.1 mM EDTA, pH 7.0. The concentrations of DNA, PNA, AP-PNA and GP-PNA oligomers were 2 µM each. The samples were first heated to 90° C. for 5 min, followed by gradually cooling to room temperature prior to measurement. UV-absorption was monitored at 260 nm from 85 to 15° C. at the rate of 0.5° C. per minute.

The concentrations of PNAs were quantified by measuring the absorbance ($A_{260}$) of the PNA solution at 260 nm. The value for the molar extinction coefficients ($\epsilon_{260}$) of the single base is: $\epsilon_{260}$ (A)=13.7 mL/(µmole·cm), $\epsilon_{260}$ (C)=6.6 mL/(µmole×cm), $\epsilon_{260}$ (G)=11.7 mL/(µmole×cm), $\epsilon_{260}$ (T)=8.6 mL/(µmole×cm) as recommended by Panagene, http://www.panagene.com/source/?doc=Support_Me01_04). Molar extinction coefficient of PNA is represented as the sum of those of individual bases that comprise the oligomer. $\epsilon_{260}=\Sigma \epsilon_i \times n_i$ ($\epsilon_i$=molar extinction coefficient of base, $n_i$=number of base).

CD spectra were recorded on an Applied™ photophysics Chirascan spectrophotometer. Each spectrum is the average of five scans, recorded at 25° C. at a 1 mm optical path length. The samples were kept in a buffer solution containing 100 mM NaCl, 10 mM sodium phosphate, and 0.1 mM EDTA, pH 7.0. The samples were heated at 90° C. for 5 min, followed by gradually cooling to room temperature prior to recording CD spectrum.

Culture and transfection of Hela cells with fluorescein-labeled aegPNA, AP-PNA, GP-PNA oligomers and Tat peptide were carried out according to previously published protocols (Janowski, B. A., et al., Nature Protocols (2006) 1, 436; Shiraishi, T., &. Nielsen, P. E., Nature Protocols (2006) 1, 633). Hela cells were grown in 75-$cm^2$ culture flasks at 37° C. in an atmosphere of 5% $CO_2$ in Hyclone DMEM/High Glucose medium without antibiotics and were plated at 100,000 cells per well on 6-well Lab-Tek chambered coverglass slides in DMEM medium and cultured two days before transfection. Oligomer solutions were prepared by diluting a 200 µM stock solution at 1×PBS buffer to 0.5 µM with warmed (37° C.) medium. The cell medium was discarded and cells were washed with 1×PBS buffer followed by incubation with the above prepared oligomers at a concentration of 0.5 µM for 24 h at 37° C. in an atmosphere of 5% $CO_2$. The medium was removed and cells were washed with 1×PBS buffer (2 mL×3) and fixed with 37% paraformaldehyde. The cells were imaged with Olympus IX51 fitted with Cool SNAP$^{HQ}$ camera and analyzed using Metamorph software (Molecular Devices).

Monomer Synthesis $N^4$-Benzoylcytosine (6). Benzoyl chloride (2.3 mL, 20 mmol) was added dropwise over 30 min to a stirred suspension of cytosine (1.1 g, 10 mmol) in dry pyridine, and stirring was continued at room temperature for a further 4 h at room temperature. The reaction was quenched by adding a small amount of methanol. The solid was filtered, washed with EtOH and dried in vacuo to give 1.92 g of the desired product 6 (90%).

1-Ethoxycarbonylmethyl-$N^4$-benzoyl cytosine (7). To a stirred suspension of 6 (1.92 g, 9 mmol) in dry DMF (100 mL) at 0° C., NaH (0.43 g, 18 mmol) was added and the mixture was stirred at room temperature for 1 h. Ethyl bromoacetate (1.5 g, 9 mmol) was added dropwise at 0° C. and stirred for 1 h. Methanol (2 mL) was added to quench the reaction, and the solvents were removed under reduced pressure. The residue obtained was dissolved in DCM, washed with water (3×50 mL), dried over $Na_2SO_4$, and the solvent was evaporated to give 7 as a white solid (1.38 g, 54%).

1-Carboxymethyl-$N^4$-benzoyl cytosine (3). Compound 7 (1.38 g, 4.6 mmol) and NaOH (0.36 g, 9.2 mmol) were dissolved in water (10 mL) and the solution was stirred at room temperature for 2 h. Then the pH was adjusted to 3 using 1M HCl. The precipitate formed was separated by filtration, washed with 5 mL water and dried in vacuo to afford 3 as a white solid (1.16 g, 92%); ESI-MS m/z 274 [M+H]$^+$; $^1H$ NMR (400 MHz, $D_2O$, sodium salt): δ7.78 (d, 1H, J=7.2 Hz), 7.75 (d, 2H, J=7.2H), 7.55 (t, 1H, J=7.2 Hz), 7.39 (t, 2H, J=7.2 Hz), 7.19 (d, 1H, J=7.2 Hz), 4.31 (s, 2H).

$N^6$-Benzoyladenine (8). Benzoyl chloride (1.3 mL, 11 mmol) was added dropwise over 30 min to a stirred suspension of adenine (1.35 g, 10 mmol) in dry pyridine, and stirring was continued at 100° C. for a further 3 h, and the reaction mixture was allowed to stand overnight at room temperature. The reaction was quenched with methanol and the solvents were removed under reduced pressure. The residue was triturated in hot isopropanol and dried in vacuo to give 8 as a white solid: yield 2.15 g (90%); MS (+ESI): m/z 240 [M+H]$^+$; $^1$H NMR (400 MHz, d-DMSO): δ11.50 (s, 1H), 8.74 (s, 1H), 8.52 (s, 1H), 8.11 (d, 2H, J=7.2 Hz), 7.66 (t, 1H, J=7.2 Hz), 7.58 (t, 2H, J=7.2 Hz).

N$^6$-Benzoyl-9-ethoxycarbonylmethyladenine (9). Compound 8 (2.39 g, 10 mmol) was dissolved in dry DMF (100 mL), cooled to 0° C., sodium hydride (0.48 g, 20 mmol) was added, and the mixture stirred at room temperature for 30 min. Ethyl bromoacetate (1.22 mL, 11 mmol) was added dropwise for 1 h. Stirring was continued for 2 h at room temperature and the reaction was quenched with methanol (2 mL). The solvents were evaporated under reduced pressure. The residue was subjected to column chromatography (DCM/MeOH; 9.5/0.5) to obtain 9 as a white solid: yield 1.3 g (40%); MS(+ESI): m/z 326 [M+H]$^+$; $^1$H NMR (400 MHz, CDCl$_3$): δ9.02 (s, 1H), 8.83 (s, 1H), 8.11 (s, 1H), 8.05 (d, 2H, J=7.2 Hz), 7.62 (t, 1H, J=7.2 Hz), 7.54 (t, 2H, J=7.2 Hz), 5.06 (s, 2H), 4.31 (q, 2H, J=7.2 Hz), 1.38 (t, 3H, J=7.2 Hz); $^{13}$C NMR (400 MHz, CDCl$_3$): δ=166.76, 164.53, 152.96, 152.50, 149.83, 143.22, 133.68, 132.80, 128.89, 127.85, 122.56, 62.53, 44.33, 14.09.

N$^6$-Benzoyl-9-carboxymethyladenine (4). Compound 9 (1.63 g, 5 mmol) and NaOH (0.4 g, 10 mmol) were dissolved in water (20 mL) and the solution was stirred for 2 h at room temperature. The pH was adjusted to 3 using 1M HCl, causing precipitation of the product. The precipitate was separated by filtration, washed with water, and dried in vacuo to give 4 as a white solid: yield 1.4 g (95%); MS(+ESI): m/z 298 [M+H]$^+$; $^1$H NMR (400 MHz, d-DMSO): δ11.682 (s, 1H), 9.11 (s, 1H), 8.81 (s, 1H), 8.52 (s, 1H), 8.09 (d, 2H, J=7.2 Hz), 7.67 (t, 1H, J=7.2 Hz), 7.60 (t, 2H, J=7.2 Hz), 5.16 (s, 2H); $^{13}$C NMR (400 MHz, CDCl$_3$): δ169.43, 166.34, 152.89, 152,09, 150.29, 145.63, 133.74, 132.98, 128.45, 122.56, 44.88.

N$^2$-isoButyrylguanine (10). Isobutyryl chloride (2.02 mL, 19.9 mmol) was added dropwise to a stirred suspension of guanine (3.02 g, 20 mmol) and TEA (1.45 mL, 10.4 mmol) in anhydrous pyridine (40 mL). The mixture was stirred for 3 h at 100° C. The reaction was quenched using methanol, and the solid was filtered, washed with methanol and dried in vacuo to give 10: yield 2.67 g (60%); MS (+ESI): m/z 222 [M+H]$^+$.

N$^2$-isoButyryl-9-ethoxycarbonylmethylguanine (11). Compound 10 (2.21 g, 10 mmol) and Na$_2$CO$_3$ (2.12 g, 20 mmol) were suspended in dry DMF, and the mixture was warmed to 80° C. with stirring. After 1 h the heating was terminated, and the reaction mixture was cooled to 0° C. and ethyl bromoacetate (1.22 mL, 11 mmol) was added dropwise for 1 h. The stirring was continued for an additional 2 h. The reaction mixture was filtered and the solid was washed with DCM. The filtrate was concentrated under reduced pressure. The residue was subjected to column chromatography ((DCM/MeOH; 9.5/0.5) to obtain 11 as a white solid: yield 0.77 g (25%); MS(+ESI): m/z 308 [M+H]$^+$; $^1$H NMR (400 MHz, CDCl$_3$): δ11.99 (s, 1H), 8.50 (s, 1H), 7.71 (s, 1H), 4.80 (s, 2H), 4.26 (q, 2H, J=6.8 Hz), 2.70 (septet, 1H, J=6.8 Hz), 1.31 (t, 3H, J=6.8 Hz), 1.28 (d, 6H, J=6.8 Hz); $^{13}$C NMR (400 MHz, CDCl$_3$): δ178.3, 166.9, 155.4, 148.5, 147.6, 139.2, 120.8, 62.3, 44.5, 36.5, 18.9, 14.1.

N$^2$-isoButyryl-9-carboxymethylguanine (5). Compound 11 (3.07 g, 10 mmol) and NaOH (0.8 g, 20 mmol) were dissolved in water (20 mL). The mixture was stirred at room temperature for 2 h. The pH was adjusted to 3 using 1M HCl, to obtain a white precipitate. The solution was filtered off, and the precipitate was washed with a small amount of cold water and dried in vacuo to give 5 as a white solid: yield 2.65 g (95%); MS(+ESI): m/z 280 [M+H]$^+$; $^1$H NMR (400 MHz, d-DMSO): δ13.32 (s, 1H), 12.06 (s, 1H), 11.64 (s, 1H), 7.93 (s, 1H), 4.88 (s, 2H), 2.74 (septet, 1H, J=6.8 Hz), 1.10 (d, 6H, J=6.8 Hz); $^{13}$C NMR (400 MHz, CDCl$_3$): δ180.63, 169.52, 155.29, 149.47, 148.52, 140.78, 120.17, 44.88, 39.38, 19.33.

N-1-Boc-1,6-diaminohexane (12). Di-tert-butyl bicarbonate (12.3 g, 0.056 mol) dissolved in 100 mL DCM was added dropwise to a solution of 1,6-diaminohexane (33 g, 0.28 mol) in 150 mL DCM during 4 hours with vigorous stirring at 0° C. The reaction was stirred for additional 20 hours at room temperature and was then washed with water (4×100 mL). The organic phase was dried over Na$_2$SO$_4$, evaporated to dryness under reduced pressure to give 14.3 g colorless oil. The data can be found in this literature (Muller, D., et al., J Org Chem 1997, 62, 411).

1-[N-Fmoc-N-(6-N-Boc-hexyl)]aminopropane-2,3-diol (14). Glycidol (4.85 mL, 73 mmol) in THF was added to the solution of 12 (14.3 g, 66 mmol) in THF dropwise at room temperature. The reaction was stirred at room temperature for 2 days. THF was removed under reduced pressure and the solid precipitate 13 was filtered and washed with DCM. The filtration was concentrated and used to the next step without any purification. FmocOSu (16.8 g, 0.05 mol) was added portionwise to a solution of the 13 in DCM at 0° C. for a period of 3 h. TEA (7 mL, 0.05 mol) was added during FmocOSu addition. The mixture was stirred at 0° C. for 2 h and was warmed to room temperature overnight. DCM was removed under reduced pressure. The residue was extracted by DCM (100 mL)/H$_2$O (100 mL). The organic phase was washed with brine and dried over sodium sulfate. It was purified by flash column chromatography; the product was obtained as a white solid (9.7 g, 28%). $^1$H NMR (CDCl$_3$): 7.68 (d, 2H), 7.48 (d, 2H), 7.32 (t, 2H), 7.23 (t, 2H), 4.51 (d, 2H), 4.14 (t, 1H), 3.64-2.87 (m, 14H), 1.37 (s, 9H); $^{13}$C NMR (CDCl$_3$): 172.3, 158.5, 143.9, 141.4, 127.7, 127.1, 124.6, 120.0, 70.8, 67.1, 63.4, 49.9, 48.8, 47.4, 40.5, 29.9, 28.4, 28.1, 26.3, 25.4.

Methyl N-{2-[N-Fmoc-N-(6-N-Boc-aminohexyl)]aminoethyl}glycinate (16). Compound 13 (2.5 g, 4.87 mmol) was dissolved in THF/H$_2$O (10 mL, 5/1) followed by the addition of sodium periodate (1.15 g, 5.36 mmol) in one portion. The mixture was sonicated in normal ultra sonic for 15 min and stirred for another 30 min at room temperature. The solid was then removed by filtration, and the filtrate was concentrated and extracted by DCM/H$_2$O. The organic phase was washed with brine, dried over sodium sulfate, and concentrated under reduced pressure. It was then dissolved in THF (4 mL) and added portion wise to the solution of glycine methyl ester hydrochloride (611 mg, 5.36 mmol) in MeOH which was neutralized to pH 7 by Et$_3$N (678 µL) at room temperature. It was stirred at room temperature for 1 hour. Sodium cyanoborohydride (918 mg, 14.61 mmol) was added to the above solution portion wise at 0° C., followed by the addition of acetic acid (279 µL, 4.87 mmol). It was stirred for 6 hours at room temperature. H$_2$O (10 mL) was added to quench the reaction. The organic solvent was removed under reduced pressure, the residue was extracted by EtOAc/H$_2$O, and the organic phase was washed with brine and dried over sodium sulfate. After removing the solvent, the product was purified by flash chromatography as pale yellow sticky oil in 1.32 g (49%); MS (M+H$^+$): 554.53; $^1$H NMR (CDCl$_3$): 7.67 (d, 2H), 7.48 (d, 2H), 7.31 (t, 2H), 7.23 (t, 2H), 4.45 (d, 2H), 4.14 (t, 1H), 3.69 (s, 3H), 3.16 (m, 2H), 2.98 (m, 4H), 1.36 (s, 9H), 1.35-1.13 (m, 12H); $^{13}$C NMR (CDCl$_3$): 172.7, 166.8, 156.0, 143.8, 141.4, 127.7, 127.1, 124.7, 120.0, 79.1, 67.4, 53.1, 48.4, 47.9, 47.3, 44.5, 40.4, 29.1, 28.4, 28.3, 26.4.

General Procedure for the Synthesis of the AP-PNA Monomer (Ester Form) 17T, 17C, 17A, 17G 16 (554 mg, 1 mmol) was dissolved in DMF (3 mL), the carboxymethyl nucleobase (1 mmol) was added, followed by the addition of NMM (4 mmol) and HATU (1.5 mmol) at 0° C. The reaction was stirred at room temperature overnight. The reaction mixture was then poured into cold water (40 mL) to form a white precipitation. The precipitation was filtered out and washed by water and hexane to give the pure methyl ester product as a white solid.

17T: yield: 94%; $^1$H NMR (CDCl$_3$): 7.68 (d, 2H), 7.48 (d, 2H), 7.32 (t, 2H), 7.24 (t, 2H), 6.91 (s, 1H), 4.54-4.44 (m, 4H), 4.13 (t, 1H), 3.71 (s, 2H), 3.64 (s, 3H), 3.40-2.89 (m, 8H), 1.82 (t, 3H), 1.38 (s, 9H), 1.42-1.00 (m, 8H); MS (M+Na$^+$): 743.57.

17A: yield: 92%; $^1$H NMR (CDCl$_3$): 8.64 (s, 1H), 8.07 (s, 1H), 7.94 (d, 2H), 7.66 (d, 2H), 7.47 (d, 2H), 7.43-7.19 (m, 7H), 4.61-4.52 (m, 4H), 4.13 (t, 1H), 3.73 (s, 3H), 3.40-2.98 (m, 10H), 1.35 (s, 9H), 1.91-1.00 (m, 8H); MS (M+H$^+$): 833.38.

17C: yield: 90%; $^1$H NMR (CDCl3): 7.80 (d, 2H), 7.64 (d, 2H), 7.62-7.19 (m, 10H), 4.73-4.07 (m, 6H), 3.61 (s, 3H), 3.57 (s, 2H), 3.53-2.67 (m, 8H), 1.31 (s, 9H), 1.71-0.95 (m, 8H); MS (M+Na$^+$): 831.56.

17G: yield: 92%; $^1$H NMR (CDCl$_3$): 7.67 (d, 2H), 7.55 (s, 1H), 7.49 (d, 2H), 7.37 (t, 2H), 7.28 (t, 2H), 4.48-3.94 (m, 5H), 3.71 (s, 2H), 3.67 (s, 3H), 3.67-2.71 (m, 9H), 1.35 (s, 9H), 1.31-1.13 (m, 14H); MS (M+H$^+$): 815.12.

General Procedure for the Synthesis of the AP-PNA Monomer (Acid Form) 18T, 18C, 18A, 18G The monomer methyl ester (1 mmol) were dissolved in a mixture of THF (3 mL) and H$_2$O (1 mL) at 0° C. NaOH (2 M, 2 mmol) was added dropwise and stirred at that temperature for 20 min. After the reaction was complete, the mixture was adjusted to pH 5 by the carefully addition of potassium hydrogen sulfate solution (1M). THF was removed under reduced pressure, the residue was extracted by ethyl acetate (30 mL×3). The combined organic phase was dried over sodium sulfate and concentrated under reduced pressure. The product was obtained after freeze-drying as white or pale yellow powder.

18T: yield: 90%; $^1$H NMR (CDCl$_3$): 7.68 (d, 2H), 7.49 (d, 2H), 7.31 (t, 2H), 7.23 (t, 2H), 6.91 (s, 1H), 4.48-4.04 (m, 5H), 3.46-2.99 (m, 10H), 1.97 (t, 3H), 1.37 (s, 9H), 1.38-0.81 (m, 8H); MS (M+H$^+$): 705.95.

18A: yield: 88%; $^1$H NMR (CDCl$_3$): 8.57 (s, 1H), 8.08 (s, 1H), 7.89 (d, 2H), 7.64 (d, 2H), 7.45 (d, 2H), 7.36-7.19 (m, 7H), 4.44-4.11 (m, 6H), 3.67 (s, 2H), 3.38-2.97 (m, 8H), 1.35 (s, 9H), 1.96-0.80 (m, 8H); MS (M+H$^+$): 819.26.

18C: yield: 85%; $^1$H NMR (CDCl$_3$): 7.82 (d, 2H), 7.66 (d, 2H), 7.64-7.19 (m, 10H), 4.73-4.07 (m, 6H), 3.61 (s, 3H), 3.57 (s, 2H), 3.53-2.67 (m, 8H), 1.31 (s, 9H), 1.71-0.95 (m, 8H) $^{13}$C NMR (CDCl$_3$): MS (M+H$^+$): 795.14.

18G: yield: 84%; $^1$H NMR (CDCl$_3$): 7.77-7.19 (m, 9H), 4.48-3.98 (m, 5H), 3.88-2.94 (m, 11H), 1.34 (s, 9H), 1.82-1.80 (m, 14H); MS (M+H$^+$): 801.18.

t-Butyl N-[2-(N-9-fluorenylmethoxycarbonyl)aminoethyl]glycinate hydrochloride (19) t-Butyl bromoacetate (7.5 ml, 31 mmol) in dry DCM (10 mL) was added dropwise to a solution of ethylenediamine (30 mL, 450 mmol) at 0° C. over 1.5 h. The resulting mixture was stirred at 0° C. for 3 h at room temperature for 18 h. The reaction mixture was diluted with DCM (20 mL), washed with brine (20 mL) [caution: the product is also soluble in water] which was re-extracted with DCM (3×20 mL). The combined organic layer was washed with brine (20 mL). TLC (colored by nihydrin) shows ethylenediamine was gone. The organic layer was dried and removed to get 7.55 g (85%) as yellow oil. The yellow oil was dissolved in DCM (25 mL) and TEA (6 mL) was added. To this solution was added dropwise a solution of Fmoc-Cl (11.2 g) in DCM (50 mL) at 0° C. over a period of 2 h. After addition, the reaction was allowed to stir at room temperature for a further 12 h. The resulting solution was washed with 1M HCl (2×50 mL) and brine (50 mL). The organic layer was dried and removed to get light yellow oil. Cooling (−20° C.) overnight resulted in a precipitate which was collected by filtration and washed with DCM until the solid was colourless. The filtrate was concentrated and cooled to get more solid. The entire combined solid was dried under vacuum to give 1 as a white solid in 5.53 g, yield 45%. MS(+ESI): m/z 396.92 [M+H]$^+$; $^1$H NMR (400 MHz, DMSO): δ9.20 (s, 2H), 7.94 (d, 2H, J=7.2 Hz), 7.73 (d, 2H, J=7.2 Hz), 7.57 (t, 1H, J=5.2 Hz), 7.46 (t, 2H, J=7.2 Hz), 7.37 (t, 2H, J=7.2 Hz), 4.38 (d, 2H, J=6.4 Hz), 4.27 (t, 1H, J=6.4 Hz), 3.91 (s, 2H), 3.37 (t, 2H, J=6 Hz), 3.03 (t, 2H, J=6 Hz). $^{13}$C NMR (400 MHz, DMSO): δ=166.27, 156.77, 144.27, 141.22, 128.32, 127.55, 125.59, 120.13, 83.50, 66.06, 47.79, 47.12, 46.89, 37.11, 28.09.

General Procedure for the Synthesis of the aegPNA Monomer (Ester Form) 19T, 19C, 19A, 19G Base-acetic acid (1 eq) was dissolved in dry DMF, HATU (1.5 eq) and NMM (5 eq) was added. The yellow green mixture was stirred at 0° C. for 10 min. Compound 1.HCl (1 eq) was added in one portion and continued to stir at 0° C. for 30 min. The reaction was allowed to stir at room temperature for 22 h. The progression of the reaction was monitored by HPLC and ESI MS. After consumption of the starting material, the reaction mixture was concentrated in vaccuo and the residue was diluted with DCM, which was washed with 1M HCl (3×30 ml) to adjust the pH to 6~7 and brine (1×30 ml). The organic layer was dried and removed to get a yellow oil which was subject to flash column chromatography [DCM/MeOH=9.5/0.5]. The ester was isolated as a white solid.

General Procedure for the Synthesis of the aegPNA Monomer (Acid Form) 20T, 20C, 20A, 20G The ester was treated with 5 mL 95% TFA at 0° C. for 30 min. The mixture was continued to stir for 12 h while warming to room temperature. The progression of the reaction was monitored by HPLC and ESI-MS. After consumption of the starting material, TFA was removed and the residue was separated with DCM/H$_2$O, and the water layer was re-extracted with DCM (3×30 ml), the combined DCM layer was washed with water (2×50 ml) and brine (1×50 ml), respectively. The organic solvent was removed and the residue was dried under vacuum to give the acid as a white solid.

20T: MS(+ESI) 506.89 [M+H]$^+$, 529.10 [M+Na]$^+$; $^1$H NMR (400 MHz, DMSO): δ11.23 (s, 1H), 7.81 (d, 2H, J=7.2 Hz), 7.61 (d, 2H, J=7.2 Hz), 7.34 (m, 3H), 7.25 (m, 2H), 7.24 (s, 1H), 4.57 (s, 1.2H), 4.40 (s, 0.8H), 4.25 (d, 2H, J=6.4 Hz), 4.13 (t, 1H, J=6.4 Hz), 2.66-3.27 (m, 4H), 1.66 (s, 3H). $^{13}$C NMR (400 MHz, DMSO): δ=171.24, 170.88, 168.08, 167.68, 164.86, 156.79, 156.54, 151.45, 144.33, 142.58, 141.20, 128.09, 127.54, 125.60, 120.59, 108.53, 65.96, 49.47, 48.14, 47.19, 12.37.

20C: MS(+ESI) 595.99 [M+H]$^+$; $^1$H NMR (400 MHz, DMSO): δ11.26 (s, 1H), 7.37-8.08 (m, 17H), 4.93 (s, 1.2H), 4.75 (s, 0.8H), 4.35-4.41 (m, 3H), 4.07 (s, 2H), 2.72-3.10 (m, 4H). $^{13}$C NMR (400 MHz, DMSO): δ=171.23, 170.89, 167.51, 167.12, 163.75, 156.83, 156.54, 151.65, 144.36, 141.21, 133.66, 133.16, 128.90, 128.08, 127.54, 125.61, 120.59, 96.19, 65.98, 50.10, 48.20, 47.37, 47.18.

20A: MS(+ESI) 620.18 [M+H]$^+$; $^1$H NMR (400 MHz, DMSO): δ11.26 (s, 1H), 7.37-8.08 (m, 17H), 4.93 (s, 1.2H), 4.75 (s, 0.8H), 4.35-4.41 (m, 3H), 4.07 (s, 2H), 2.72-3.10 (m, 4H). $^{13}$C NMR (400 MHz, DMSO): δ=171.28, 170.77, 167.38, 166.90, 156.90, 156.61, 151.96, 145.97, 144.32, 141.21, 133.76, 132.98, 128.96, 128.08, 127.52, 125.57, 120.60, 65.98, 49.64, 48.18, 47.42, 47.20, 44.76.

20G: MS(+ESI) 602.15 [M+H]$^+$; $^1$H NMR (400 MHz, DMSO): δ11.98 (s, 1H), 11.56 (s, 0.5H), 11.49 (s, 0.5H), 7.24-7.82 (m, 10H), 4.04 (s, 1.2H), 4.88 (s, 0.8H), 4.16-4.29 (m, 3H), 3.94 (s, 2H), 2.26-3.42 (m, 5H), 1.03 (d, 6H, J=6.0 Hz). $^{13}$C NMR (400 MHz, DMSO): δ=180.59, 171.26, 170.85, 167.46, 166.92, 156.84, 155.334, 148.37, 144.32, 141.23, 128.07, 127.51, 125.57, 125.50, 120.59, 65.97, 48.30, 47.38, 47.20, 44.55, 35.12, 19.31.

Oligomer Synthesis

General Procedure for AP-PNA Oligomer Assembling

PNA oligomers were assembled on a Rink amide PEGA resin using Fmoc/acyl/Boc or Fmoc/Bhoc/Boc protecting group strategy. 50 mg Fmoc-Rink amide PEGA resin was swollen with 3 mL DMF/DCM (5/1) for 2 h. The Fmoc group was deprotected by 20% piperidine in DMF and shaking the reaction vessel for 5 min (repeated twice). Resin was washed with DMF, DCM and was monitored with Kaiser test. The monomer (aegPNA or AP-PNA) were activated using the following two methods. Method A: monomer (2 eq), PyBOP (2 eq) and DIEA (10 eq) and method B: monomer (2 eq), HATU (2 eq) and DIEA (10 eq) for 5 min at room temperature. When the coupling of the incoming monomer was onto a primary amine, i.e., to an aegPNA monomer, method A was used. Otherwise, when the incoing monomer was coupled to a secondary amine, i.e., to an AP-PNA monomer, method B was used. The activated mixture was added directly to the Fmoc-deprotected resin and the mixture was shaked for 4 or 5 h at room temperature, followed by washing DMF/DCM and check by ninhydrin test. The Fmoc deprotection and monomer coupling cycle was repeated until the full the sequence was assembled. After the final Fmoc deprotection, the terminal amine was capped by adding 5% acetic anhydride in DMF and the mixture shaked for 15 min. The resin was washed thoroughly with DMF/DCM and dried under vacuo. Cleavage from the resin was carried out by adding 2 mL 95% TFA (2.5% TIS, 2.5% H$_2$O) to the dry resin and the resin suspension was shaked for 1 h at room temperature. The cleavage cocktail was filtered and the resin was washed with TFA (1 mL×2). The combined filtrate was precipitated by adding 15 mL cold diethyl ether, centrifuged to get the crude white solid. The crude white solid was lyophilized overnight. For PNA synthesized using the Fmoc/acyl/Boc protecting group strategy, the dried solid was then dissolved in 2 mL 35% ammonia solution and incubated overnight at 42° C. The ammonia solution was dried and the resulting residue was redissolved in H$_2$O and purified by semipreparative reverse-phase HPLC. For PNA synthesized using the Fmoc/Bhoc/Boc protecting group strategy, no ammonia treatment was needed and the crude product after the TFA cleavage procedure was directly subjected to HPLC purification. The expected product was detected by MALDI-TOF mass spectroscopy. The product was then lyophilized to afford a white powder. The expected and observed masses for all the AP-PNA oligomers are summarized in FIG. 10.

General Procedure for Converting an AP-PNA Oligomer to a GP-PNA Oligomer

The pure dried AP-PNA oligomer and N,N'-bisBoc-S-methylthiourea (10 eq per amino group) were dissolved in 50 μL DMF in an eppendorf tube, triethylamine (2 eq per amino group) was added to the clear solution. Some prepicitate came out which was the TEA/TFA salt. Then the mixture was let stand overnight at 42° C. DMF was removed by lyophilization and the dry residue was washed with hexane (30 μL*3) to remove excess N,N'-bisBoc-S-methylthiourea. The resulting mixture was then treated with 95% TFA at room temperature for 1 h, which was then diluted with H$_2$O and subjected to purification by semipreparative reverse-phase HPLC. The expected product was dected by MALDI-TOF mass spectroscopy. The HPLC fractions were lyophilized to afford a white powder. The expected and observed masses for all the GP-PNA oligomers are also summarized in FIG. 10.

The present inventors investigated a new type of PNA in which a peptoid side chain bearing a functional headgroup is introduced at the γ-nitrogen of the aegPNA backbone. The schematic structure is shown in FIG. 1D. This modification does not generate a chiral centre, and the headgroup can be an amine or guanidine or other functional groups. The inventors' design was based on the same rationale that polycationic groups, the guanidino groups in particular, play a critical role in facilitating the cellular uptake of many cell-permeable polymeric compounds (Nagahara, H., et al., *Nat Med* (1998) 4, 1449; Wender, P. A., et al., *Proc Natl Acad Sci USA* (2000) 97, 13003) and that introducing positive charges can also increase water solubility Nielsen, (P. E., et al., *Angewandte Chemie International Edition in English* (1996) 35, 1939). So far, there has been only one reported study on γ-nitrogen-modified PNA (Haaima, G., et al., *New Journal Of Chemistry* (1999) 23, 833), in which the Nielsen group have found that γ-nitrogen methylated PNA are still able to bind to the complementary oligonucleotide target albeit with a thermal stability that is 1.5-4.5° C. lower per modified monomer unit than that of aegPNA and that the relative preference of aegPNA for binding to DNA in the antiparallel orientation is also diminished or even completely abolished for N$^γ$-methylated PNA depending on the extent of N$^γ$-methylation (Haaima, et al., 1999, supra). The present inventors have designed, synthesized and evaluated two new types of PNA analogs, aminopeptoid-PNA (AP-PNA) and guanidinopeptoid-PNA (GP-PNA), with varying lengths of the peptoid side chain. The inventors have further observed that the spacer length between the headgroup and the backbone is critically important in determining the thermal stability of these N$^γ$ modified PNAs in binding to complementary DNA, i.e., the binding affinity increases when the spacer length is increased from 2 to 6 atoms for these PNA analogs. In particular, PNA oligomers containing the 6-atom-spacer AP-PNA or GP-PNA monomers bind to antiparallel complementary DNA with a comparable thermal stability to that of unmodified aegPNA and the preferential binding to the antiparallel DNA oligonucleotide is also largely preserved. Most importantly, a dodecamer PNA with six guanidino-peptoid modifications is shown to have good cell permeability. The present inventors demonstrate the synthesis, hybridization, CD analysis and cell permeability of PNA oligomers containing one or more such AP-PNA or GP-PNA monomer units in the sequences.

Synthesis of AP-PNA (X=NH$_2$) monomers can be divided into the synthesis of the peptoid backbone 1 and the nucleobase-acetic acids 2-5, as shown in FIG. 2. The acyl protected base-acetic acids were synthesized by the method previously described in the literature (FIG. 3; Will, D. W., et al., *Tetra-* hedron (1995) 51, 12069; Timar, Z., et al., *J. Chem. Soc., Perkin Trans.* 1 (2000) 19; Finn, P. J., *Nucleic Acids Res* (1996) 24, 3357). Thymine-1-acetic acid 2 was obtained commercially. 1-Carboxymethyl-$N^4$-benzoyl cytosine 3 was prepared by reacting cytosine with benzoyl chloride to give $N^4$-benzoyl cytosine 6 which was subsequently alkylated with ethyl bromoacetate to give 7, followed by saponificative hydrolysis with acequous NaOH.

$N^6$-Benzoyl-9-carboxymethyladenine 4 was formed by reacting adenine with benzoyl chloride to give $N^6$-benzoyl adenine 8 which was alkylated with ethyl bromoacetate to form two isomers, the $N^7$-isomer and $N^9$-isomer 9 in a 1-to-2 ratio. The two isomers were identified by 2D NMR HMBC experiment. The regiochemical assignment of $^{13}C$ signals in substituted purines is known from INEPT experiments (Osterman, R. M., et al., *Tetrahedron Letters* (1992) 33, 4867; Hudson, R. H. E., et al., *Synlett* (2005) 1442). The $N^9$- and $N^7$-isomers can be distinguished by the cross-peaks arising from the coupling of methylene protons of the $\underline{CH_2}COOEt$ fragment with C4 and C5 carbons. For the $N^9$-isomer, the methylene protons (singlet at δ=5.07 ppm) are coupled to both C4 and C8 carbons but not to C5, while the analogous methylene protons of the $N^7$-isomer (singlet at δ=5.50 ppm) shows coupling to C5 and C8 but not to C4. The desired $N^9$-isomer 9, purified by column chromatography, was subjected to saponification conditions to yield $N^6$-benzoyl-9-carboxymethyladenine 4. $N^2$-isobutyryl-9-carboxymethylguanine 5 was synthesized and characterized in a similar way. The isobutyryl protecting group was introduced at the $N^2$-position of guanine by reacting it with isobutyryl chloride in the presence of DIEA in dry pyridine to afford 10, which was alkylated subsequently with ethyl bromoacetate to form two isomers, the $N^7$-isomer and $N^9$-isomer 11, in a 2-to-3 ratio. The desired $N^9$-isomer 11, which was identified by 2D NMR HMBC experiment, was subject to saponification conditions to give $N^2$-isobutyryl-9-carboxymethyl-guanine 5. The acyl protecting groups could be removed after oligomerization by treatment with 35% ammonium at 40° C. These have been shown compatible with both Fmoc and Boc chemistry, therefore are quite useful for the synthesis of PNA oligomers.

Figure 4:
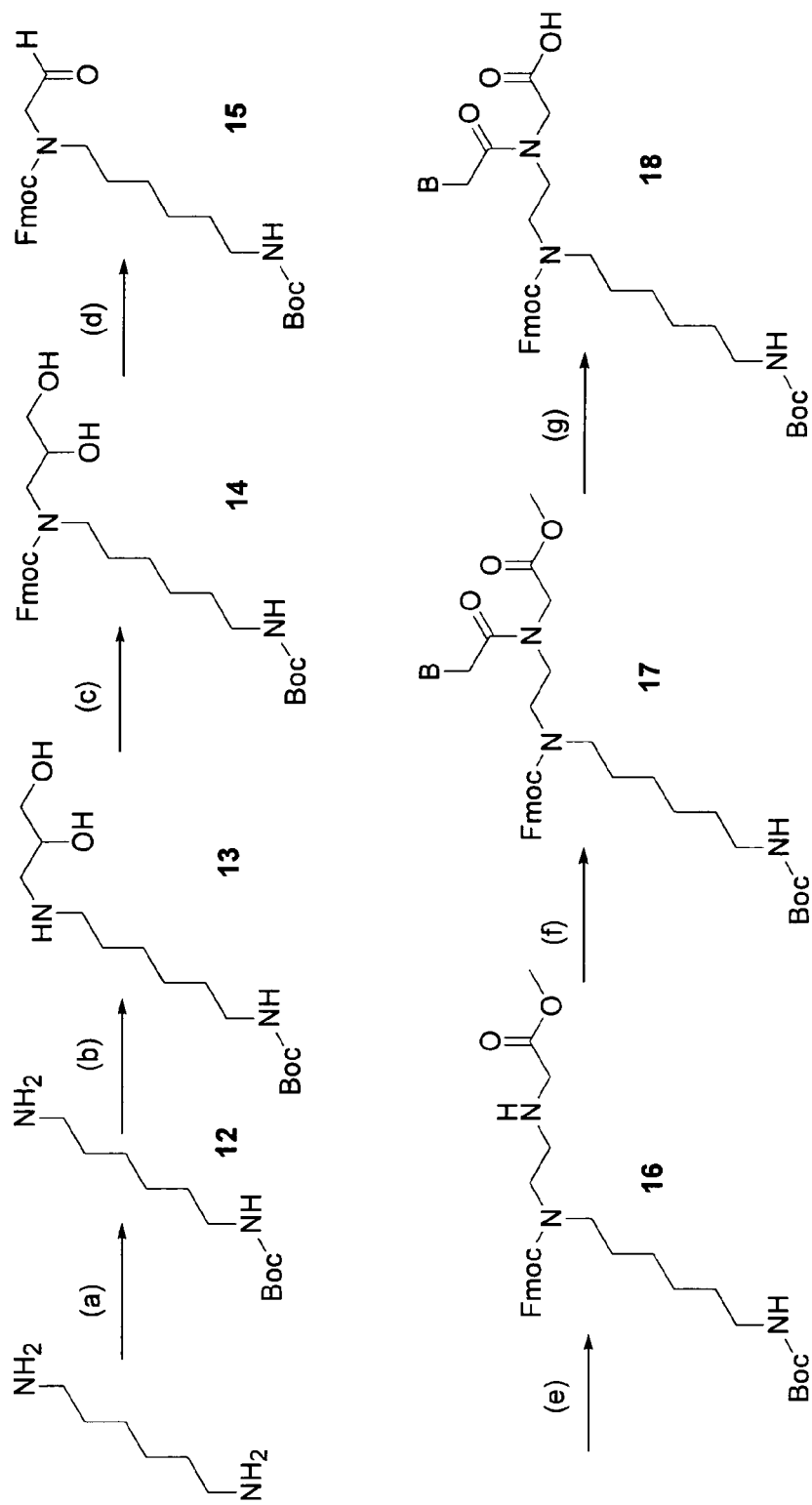
FIG. 4 depicts the synthesis of AP-PNA monomers: (a) $(Boc)_2O$, DCM, 0° C.; (b) Glycidol, THF, 45° C.; (c) Fmoc-OSu, ACN; (d) $NaIO_4$, $THF/H_2O$; (e) H-Gly-OMe, NaCNBH$_3$, THF/MeOH; (f) $BCH_2COOH$, HATU, DIEA, DMF; (g) (i) NaOH; (ii) $KHSO_4$. B=T, thymine; C, $N^4$-Benzoylcytosine; A, $N^6$-Benzoyladenine; G, $N^2$-isoButyrylguanine.
Figure 5:
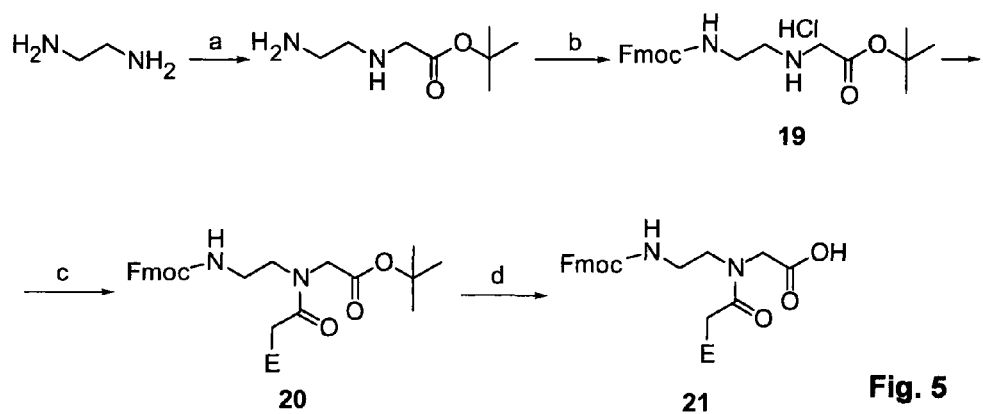
FIG. 5 shows the synthesis of a aegPNA monomer: (a) t-butyl bromoacetate, DCM; (b) i. Fmoc-Cl, TEA, DCM; ii. Dilute HCl; (c) Nucleobases, HATU, NMM, DMF; (d) 95% TFA, DCM. B=T, thymine; C, $N^4$-Benzoylcytosine; A, $N^6$-Benzoyladenine; G, $N^2$-isoButyrylguanine.
Figure 6:
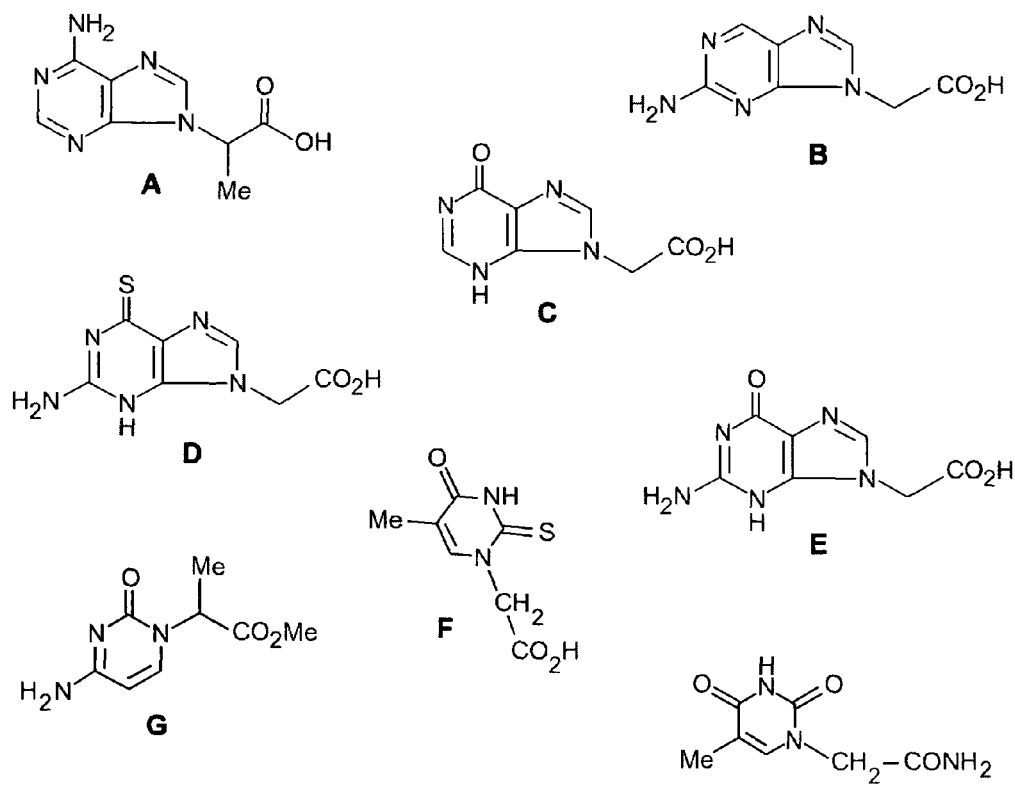
FIG. 6 depicts further examples of suitable compounds that may be used to introduce the nucleobase in order to form a PNA monomer according to the invention.

The method used by Nielsen et al. for the synthesis of N-methyl monomers (Haaima, G., et al., *New Journal Of Chemistry* (1999) 23, 833) was adapted to the synthesis of AP-PNA monomers. Shown in FIG. 4 are the reaction steps for the preparation of the AP-PNA monomers with a 6-C spacer linking the amino headgroup to the backbone. The same chemistry was used to synthesize other AP-PNA monomers with different spacer length. The Boc protecting group was selected for the peptoid side chain amine, and the Fmoc protecting group was selected for the backbone 2° amino group from which the oligomer elongates. Thus, $(Boc)_2O$ was reacted with an excess amount of 1,2-diaminohexane to form tert-butyl (6-aminohexyl)carbamate or 6-(t-Boc-amino) hexyl amine 12. Compound 12 was then reacted with glycidol to produce 13 which, after Fmoc protection of the backbone amine, was oxidatively cleaved with $NaIO_4$ to produce 15. Compound 15 was subsequently reacted with glycine methyl ester hydrochloride at neutral pH to yield the corresponding imine, which was reduced in situ with $NaBH_3CN$ to give the desired AP-PNA backbone, $N^\gamma$-(6-aminohexyl)aeg 16. Coupling the acyl-protected nucleobase-acetic acids 2-5 individually with the backbone 16 in the presence of HATU and NMM gave 17 which, after alkaline hydrolysis, yielded the four corresponding AP-PNA monomers 18.

For the synthesis of GP-PNA, the guanidino group can be introduced to the AP-PNA peptoid side-chain at the monomer stage or at the oligomer stage. If introduced at the monomer stage, special and expensive guanidine protecting groups, such as Pmc or Pbf, are needed. If introduced at the oligomer stage, one can convert the amine-deprotected polyamine AP-PNA to polyguanidine GP-PNA in good yields by treatment with excess amount of a guanylation reagent, such as N,N'-bisBoc-S-methylthiourea. In the present examples the latter were used, i.e., the global guanidination method, to synthesize the GP-PNAs.

Synthesis of the unmodified aegPNA monomer also includes two parts, the aeg linker and acyl protected nucleobases. The Fmoc-protected aeg linker was prepared according to published procedures (Thomson, S. A., et al., *Tetrahedron* (1995) 51, 6179). The aegPNA monomers were easily obtained by coupling the appropriately protected nuceleobase-aetic acids 2-5 with 19.

Oligomers Synthesis

The AP-PNA oligomers were synthesized using Rinkamide PEGA resin according to standard solid-phase Fmoc peptide synthesis protocols. The coupling reagent is either PyBOP/NMM for coupling onto an aegPNA residue or HATU/NMM for coupling onto an AP-PNA residue in NMP. After oligomer assembling, the PNA-resin was first treated with TFA to remove the Boc protecting groups from the peptoid side chain amines and cleave the oligomer from the resin, followed by treatment with 35% ammonia to remove the exocyclic nucleobase protecting groups. It was also possible to conduct the final deprotection/cleavage in the reverse order, i.e., treating the resin first with ammonium then with TFA, which was used for AP-PNA with a short (2 or 3 carbons) peptoid side chain. Of course, when Bhoc was used as a protecting group for the nucleobase, there was then no need for the ammonia treatment step. Crude AP-PNAs were purified by reversed-phase HPLC and characterized by MALDI-TOF mass spectrometry. The GP-PNA oligomers were obtained by treatment of the corresponding pure AP-PNA oligomers with excess N,N'-bisBoc-S-methylthiourea in the presence of DIEA in DMF, followed by Boc removal by TFA treatment and HPLC purification. The purified GP-PNAs were characterized by MALDI-TOF mass spectrometry.

Duplex Formation and Stability

Decamer aegPNA, AP-PNA, GP-PNA oligomers of mixed pyrimidine-purine sequences were used for studies of duplex formation with complementary anti-parallel DNA, parallel DNA and one single-base mismatched DNA as well as with complementary anti-parallel RNA and one single-base mismatched RNA. Five series of AP-PNA and GP-PNA oligomers with a peptoid spacer of 2, 3, 4, 5 or 6 carbons were synthesized in which one, two, three, four or five modified monomers were included and spaced alternately or separately with the aegPNA monomer. FIG. 7 shows the thermal stability (Tm, ° C.) of examples of the duplexes formed between these PNAs and DNA or RNA. From these data, one can see that, on the average, the series with a longer peptoid spacer (6, 5 or 4 carbon atoms) exhibit better binding affinity toward complementary DNA or RNA than do the series with a shorter spacer (3 or 2 carbon atoms). From FIG. 7A, the 6-C AP-PNA and GP-PNA series have a very comparable thermal stability in binding to the complementary DNA with that of the unmodified aegPNA. For instance, for the 6-C AP-PNAs, including 1 or 2 modified monomers in the decamer even increased slightly the thermal stability as compared to the unmodified aegPNA. Therefore, compared to N-methylation which was reported to cause a decrease in thermal stability of 1.8-4.5° C. per N-methyl unit (Haaima, G., et al., *New Journal Of Chemistry* (1999) 23, 833), N-amino- or N-guanidinohexylation did not significantly change the binding affinity of the resultant PNA to complementary DNA. One may be tempted to believe that the destabilizing effect of the N-methyl group is compensated by the presence of the positively charged headgroups on the peptoid side chains which can have electrostatic interaction with the negatively charged DNA backbone. However, removal of the positive charge(s) by N-acetylation on the two AP-PNAs (AP-PNA 6-1, AP-PNA 6-2) yielded two neutral PNAs (acAP-PNA 6-1, di-acAP-PNA 6-2) without significantly lowering the binding affinity. The Tm of acAP-PNA 6-1 with anti-parallel complementary DNA duplex was just slightly lower than that of AP-PNA 6-1, whereas the Tm of di-acAP-PNA 6-2/DNA was almost the same as that of AP-PNA 6-2/DNA. Thus, the positive charge on the peptoid side chain does not seem to play a critical role in determining the thermal stability of the PNA/DNA duplex. This interpretation is also consistent with an independent study on the γ-Lys-PNAs (Englund, E. A., & Appella, D. H., *Angewandte Chemie International Edition in English* (2007) 46, 1414). This suggests that other factors, such as hydrogen bonding and intrastrand steric interaction, might also affect the thermal stability of such PNA/DNA duplexes. For AP- and GP-PNAs, the length of the peptoid side chain seems to be very critical. Having a short peptoid side chain is detrimental to the binding affinity of these PNA analogs. One can see that the destabilization effect of N-aminoethylation or N-guanidinoethylation on PNA-DNA duplex stability is more pronounced than that of N-methylation, as a very large drop in thermal stability was observed for the AP-PNA and GP-PNA series with this shortest 2-C spacer (FIG. 7D). Taking AP-PNA2-1, for example, a single modification on the thymine at residue 6 reduced its binding affinity to complementary DNA by more than 8° C. in thermal stability compared to aeg PNA. However, when an aminopropionyl group or β-alanyl was introduced onto the peptoid amine of AP-PNA 2-1, which extended the side chain by 3 atoms (FIG. 7D, last entry), the resultant βAla-AP-PNA2-1 exhibited a binding affinity to the antiparallel DNA that is 5° C. higher in thermal stability than that of AP-PNA 2-1, illustrating again the beneficial effect of a longer spacer. Despite the negative impact of a short peptoid spacer on binding affinity, it is worth noticing that most of the AP-PNAs and GP-PNAs listed in FIGS. 7C and 7D still bind better to complementary antiparallel DNA than do the corresponding DNA oligonucleotide which has a DNA/DNA duplex thermal stability of ~33.5 (Haaima, et al., 1999, supra) and that these also bind in a sequence selective manner. The moderate binding affinity of these peptoid PNAs, such as AP- or GP-PNA3s, may be of beneficial value for antisense applications considering the extremely tight binding of unmodified PNA and the optimal length of an antisense oligo (~15-20 mer) (Meier, C., & Engels, J. W., *Angewandte Chemie International Edition in English* (1992) 31, 1008). By introducing such short-spacer peptoid modifications, one can modulate the hybridization strength of PNA to achieve sequence-specific targeting at physiological temperature.

Similar to aegPNA, the AP-PNAs and GP-PNAs also display preferential binding towards antiparallel DNA to parallel DNA. The difference in thermal stability between the two types of duplexes is rather significant in most cases. To determine the selectivity of AP-PNA and GP-PNA, the present inventors also measured the thermal stability of AP-PNA and GP-PNA in binding to antiparallel DNA containing one single-base mismatch. Although there is a distinct thermal transition of the single stranded PNA itself around 40° C., no clear or weak thermal transitions were observed for AP-PNA and GP-PNA when they were incubated with the mismatched DNA. Nevertheless, the data collected from the weak transition points showed remarkably lower thermal stability than the fully matched antiparallel DNA. This clearly shows that introducing the peptoid side chains into aegPNA does not compromise the binding selectivity and AP-PNA and GP-PNA have the ability to discriminate between closely related sequences.

Interestingly, AP-PNA and GP-PNA seem to form a more stable duplex with antisense RNA than with antisense DNA. From FIG. 7E, the melting temperatures of the PNA/RNA duplexes are generally higher than those of the corresponding PNA/DNA duplexes. Notably, for most of the duplexes formed from the 6-C or 5-C AP-PNAs and GP-PNAs, the stability is actually slightly higher than that of the aegPNA/RNA duplex. All the peptoid PNAs also display sequence-selective binding to RNA, as seen from the significantly lower Tm values of the duplexes formed with a single-base mismatched RNA.

CD Spectroscopy

Figure 8A:
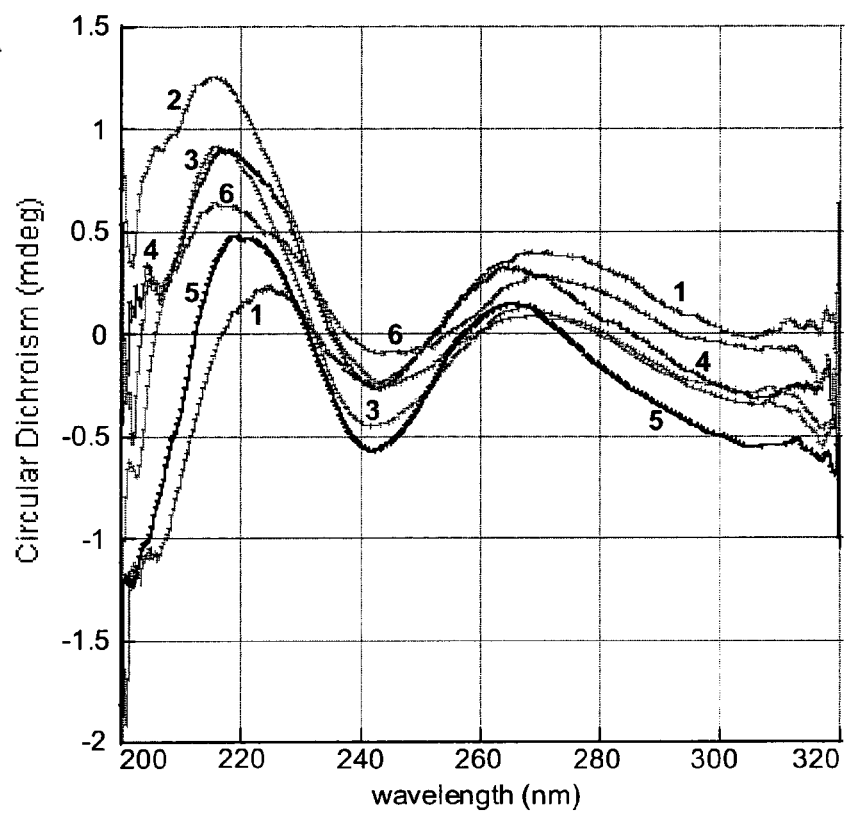
FIG. 8A: 1: aegPNA/DNA; 2: AP-PNA 6-5/DNA; 3: AP-PNA 6-4/DNA; 4: AP-PNA 6-3/DNA; 5: AP-PNA 6-2/DNA; 6: AP-PNA 6-1/DNA.
Figure 8B:
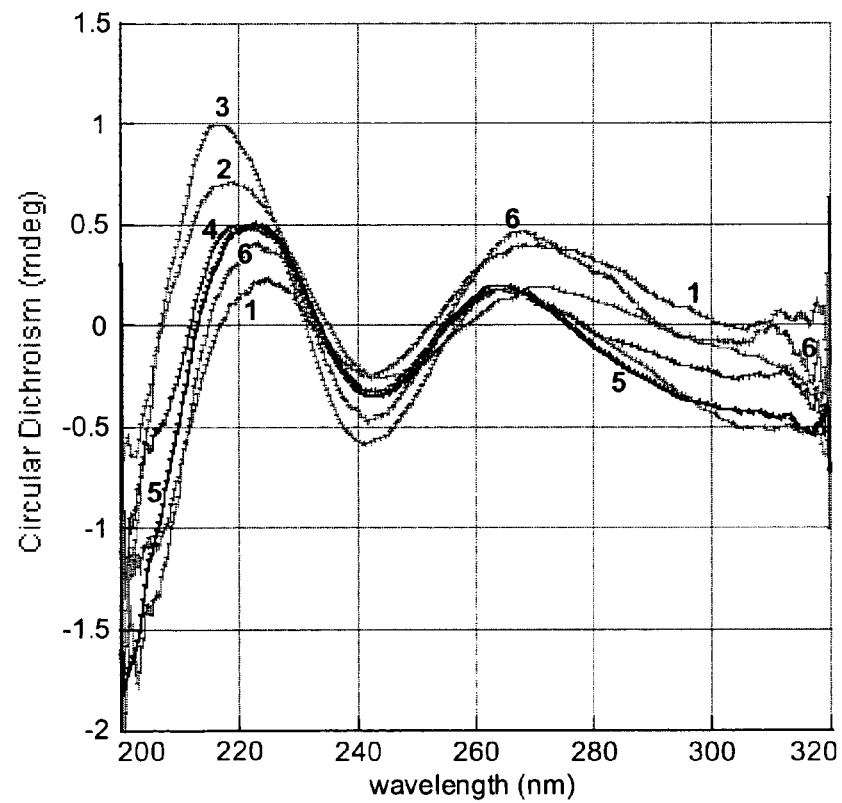
FIG. 8B: 1: aegPNA/DNA; 2: GP-PNA 6-5/DNA; 3: GP-PNA 6-4/DNA; 4: GP-PNA 6-3/DNA; 5: GP-PNA 6-2/DNA; 6: GP-PNA 6-1/DNA.

CD spectroscopy was used to examine whether the introduction of amino- or guanidinoalkyl groups on the γ-nitrogen backbone causes any changes on the structure of PNA/DNA duplexes. The results of the GP-PNA/DNA and AP-PNA/DNA duplexes from the 6-C spacer series are presented in FIG. 8. The PNAs were hybridized with the complementary anti-parallel DNA at a concentration of 6 μM and the CD spectra were recorded at 200 to 320 nm. The results presented in FIGS. 8A and 8B clearly show that all these duplex structures display a CD spectrum that closely resembles that of the aegPNA/DNA duplex, indicating no major conformational change in the AP-PNA/DNA or GP-PNA/DNA duplexes. It can thus be concluded that all these AP-PNA/DNA and GP-PNA/DNA duplexes adopt a similar right-handed helix as does the unmodified PNA/DNA duplex (Egholm, M., et al., *Nature* (1993) 365, 566; Sforza, S., et al., *European Journal of Organic Chemistry* (1999) 197-204).

Cell Uptake Study of FAM-Labeled aegPNA, APPNA, GP-PNA and TAT

Figure 9A:
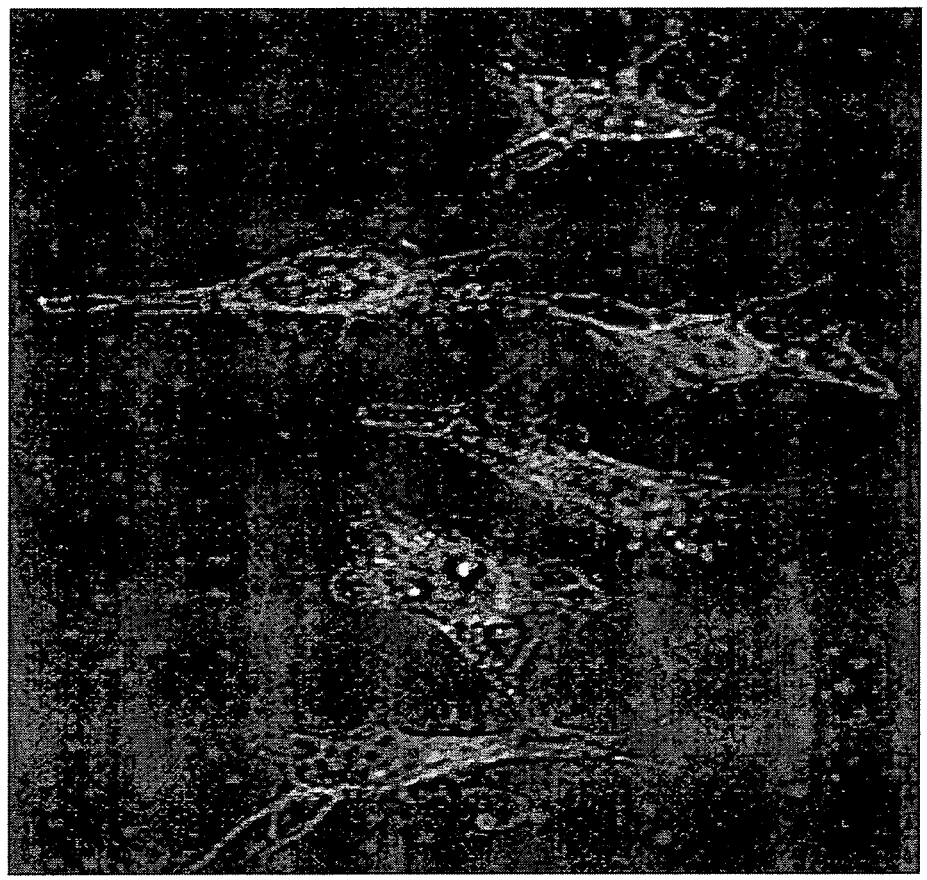
FIG. 9 depicts fluorescent confocal microscopy images of the uptake of fluorescein (FAM)-labelled aegPNA (FIG. 9A), AP-PNA (FIG. 9B), GP-PNA (FIG. 9C) and TAT domain (FIG. 9D) incubated for 24 h with Hela cells at a concentration of 0.5 μM. Overlay of DIC and fluorescent images.
Figure 9B:
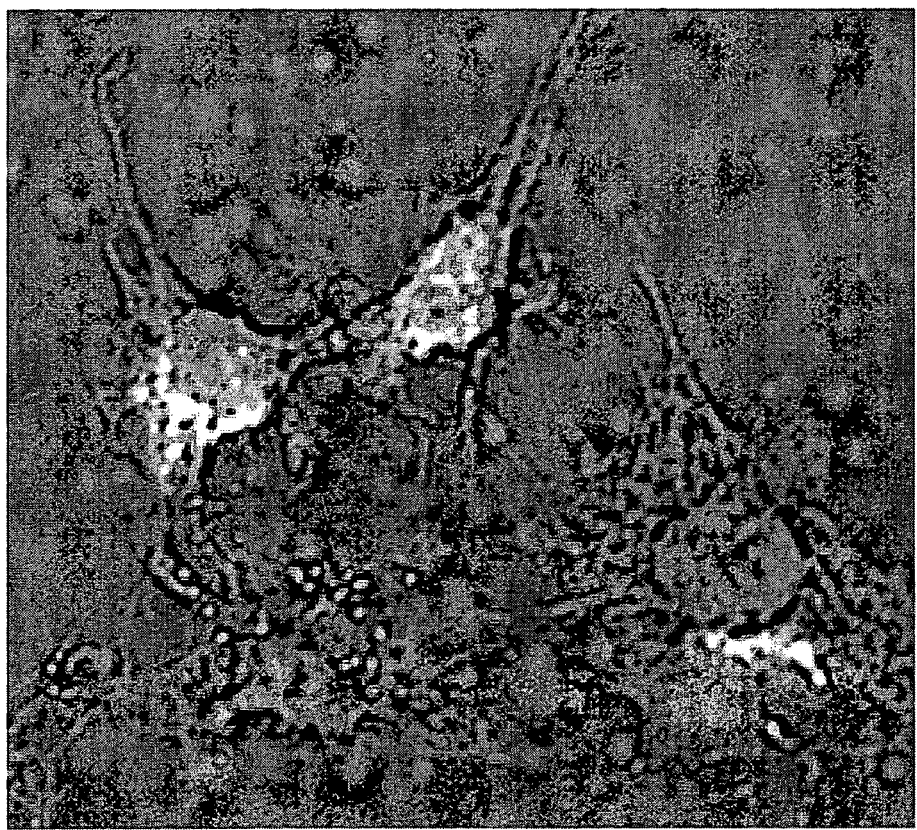
Figure 9C:
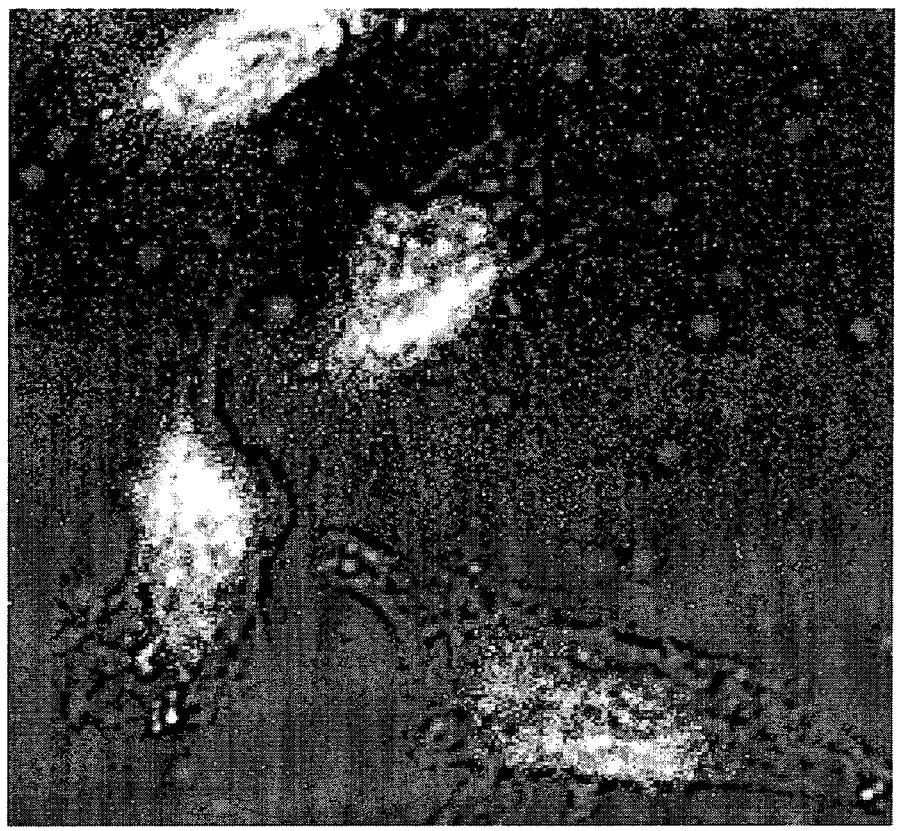
Figure 9D:
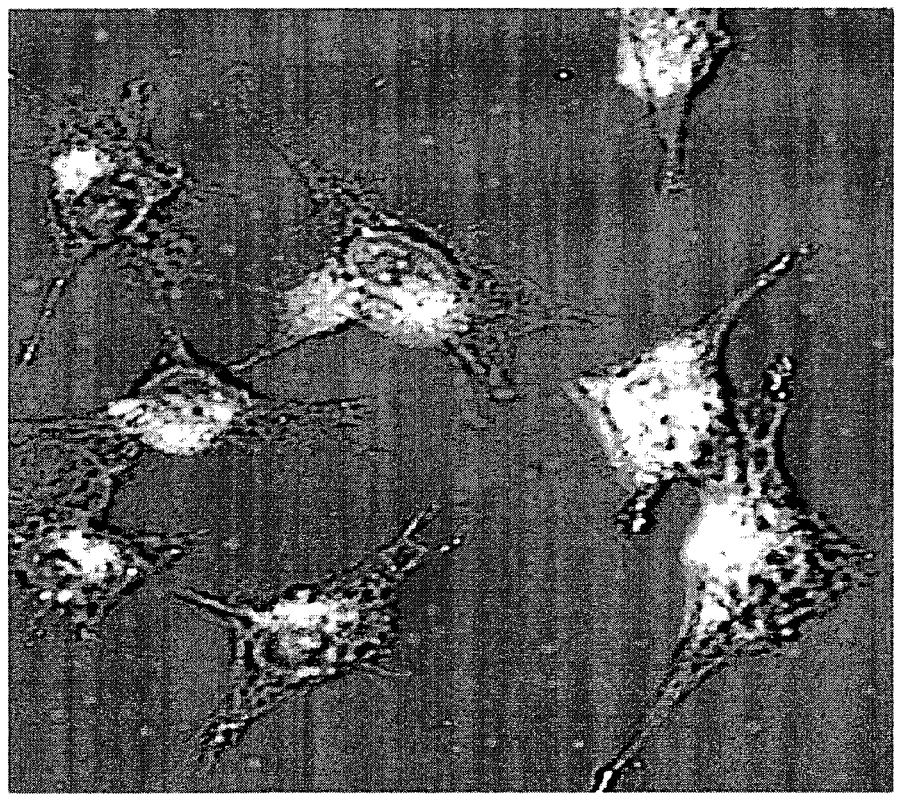

For the present example the GP-PNA and AP-PNA with the 6-C spacer was chose to examine the cell-uptake activity, since these display the strongest binding affinity when complexed to complementary DNA. Dodecamer aegPNA (Fl-TAGTAGATCACT-Gly-NH$_2$) (SEQ ID NO:1), AP-PNA (Fl-TA$^{6a}$GT$^{6a}$AG$^{6a}$AT$^{6a}$CA$^{6a}$CT$^{6a}$-Gly-NH$_2$) (SEQ ID NO:2), GP-PNA (Fl-TA$^{6g}$GT$^{6g}$AG$^{6g}$AT$^{6g}$CA$^{6g}$CT$^{6g}$-Gly-NH$_2$) (SEQ ID NO:3) oligomers and Tat peptide (Fl-Tyr-Gly-Arg-Lys-Lys-Arg-Arg-Gln-Arg-Arg-Arg-NH$_2$) (SEQ ID NO:4) were synthesized and labeled by fluorescein at the N-terminus. These oligomers were incubated with Hela cells for 24 h at 37° C. and were fixed by paraformaldehyde after PBS (1×) buffer washing. Their uptake properties were determined by fluorescence confocal microscopy. FIG. 9 shows the relative uptake efficiency of these oligomers. The aegPNA showed poor cell uptake property, where the fluorescence images in Hela cells were too faint to be detected. The AP-PNA oligomer had a better cell uptake property than the aegPNA, as the fluorescence was clearly observed inside the cells, but not all the cells had fluorescence absorbance which meant that AP-PNA did not enter all the cells. For the GP-PNA oligomer, clear and strong fluorescence images were detected in almost all cells and it crossed the cell membrane almost as effectively as did the Tat transduction peptide (FIG. 9C and FIG. 9D). To conclude, the guanidino groups pendant from the backbone amide nitrogen confer cell-permeability to the modified PNAs.

CONCLUSIONS

The present inventors have demonstrated that PNAs containing peptoid side chains on the γ-nitrogen of the aeg backbone exhibit sequence-specific binding to DNA. Interestingly, AP-PNAs and GP-PNAs with a six-methelene spacer between the headgroup and the backbone are as good as aegPNA in binding to DNA and those with a shorter spacer display decreased binding affinity. These new PNA analogs adopt the same secondary structure when complexed to DNA as does the unmodified PNA. Most importantly, the inventors have shown that GP-PNA is readily taken up by Hela cells while AP-PNA gives a moderate enhancement in cell uptake activity compared with aegPNA. These findings suggest that modifications on PNA backbone are capable of generating new cell-permeable antisense molecules of which the hybridization affinity can be modulated to meet the requirement of gene-specific targeting for in vivo applications.

The listing or discussion of a previously published document in this specification should not necessarily be taken as an acknowledgement that the document is part of the state of the art or is common general knowledge.

The invention illustratively described herein may suitably be practiced in the absence of any element or elements, limitation or limitations, not specifically disclosed herein. Thus, for example, the terms "comprising", "including," containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by exemplary embodiments and optional features, modification and variation of the inventions embodied therein herein disclosed may be resorted to by those skilled in the art, and that such modifications and variations are considered to be within the scope of this invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

Other embodiments are within the following claims. In addition, where features or aspects of the invention are described in terms of Markush groups, those skilled in the art will recognize that the invention is also thereby described in terms of any individual member or subgroup of members of the Markush group.

What is claimed is:
1. A peptide nucleic acid monomer defined by the general structural formula (I):

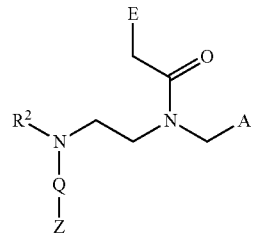

wherein Q is an aliphatic bridge having a main chain of a length from 2 to 12 carbon atoms, optionally comprising 1 or 2 heteroatoms selected from N, O, S, Se and Si, $R^2$ is one of a removable amino-protecting group, an aliphatic group, an alicyclic group, an aromatic group, an arylaliphatic group, an arylalicyclic group, a silyl-group or H, A is one of —COOH, —COOR$^3$, —COX, —COSR$^3$, —CN, —CONH$_2$, —CONHR$^3$, or —CONR$^3$R$^4$, wherein R$^3$, and in —CONR$^3$R$^4$R$^4$, are independently selected from the group consisting of H, and an aliphatic, alicyclic, aromatic, arylaliphatic, and arylalicyclic group comprising 0 to 3 heteroatoms selected from N, O, S, Se and Si, and X in —COX is a halogen atom, and E is a nucleobase, and Z is a polar head group.

2. The peptide nucleic acid monomer of claim 1, wherein the main chain of Q has a length from 4 to 8 carbon atoms.

3. The peptide nucleic acid monomer of claim 1, wherein the peptide nucleic acid monomer is defined by the general structural formula (Ic):

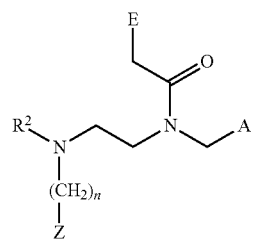

wherein n is an integer from 2 to 12.

4. The peptide nucleic acid monomer of claim 3, wherein n is selected in the range from 4 to 8.

5. The peptide nucleic acid monomer of claim 1, wherein $R^2$ is one of a carbamate group, a methylaryl group (phtaloyl, tetrachlorophtaloyl), an acetamido group, a trifluoroacetamido group, an arylsulfonyl group (p-toluolsulfonyl-), an o-nitrophenylsulfenyl group, a trifluoroacetyl group-, a trityl group-, an allyl group, a 9-phenylfluorenyl group, a dithiasuccinyl group, a triazinanone group, an N-bis(methylthio)methylene group or an N-diphenylmethylene group.

6. The peptide nucleic acid monomer of claim 5, wherein the carbamate is one of methoxycarbonyl-, ethoxycarbonyl-, benzylcarbonyl-, benzyloxycarbonyl-, nitrobenzyloxycarbonyl-, benzhydryloxycarbonyl-, allyloxycarbonyl-, tert-butoxycarbonyl-, 9-fluorenylmethoxycarbonyl-, 2-(trimethylsilyl)ethoxycarbonyl-, 2,2,2-tricholorethoxycarbonyl-, or 2-(4-trifluoromethylphenylsulfonyl)ethoxycarbonyl.

7. The peptide nucleic acid monomer of claim 1, wherein the polar head group Z is capable of carrying a charge in aqueous solution in a pH range from about 5 to about 11.

8. The peptide nucleic acid monomer of claim 7, wherein the polar head group Z is capable of carrying a positive charge in aqueous solution.

9. The peptide nucleic acid monomer of claim 8, wherein the polar head group Z is capable of carrying a positive charge under physiological conditions.

10. The peptide nucleic acid monomer of claim 1, wherein the polar head group Z is one of an amino group, an amido group, a carboxyl group, an ester group, a hydroxyl group, a thio group, a seleno group, a phosphonate group, a sulfonate group, a guanidine group or an imidazole group.

11. The peptide nucleic acid monomer of claim 1, wherein the polar head group Z is an amino group or a guanidine group.

12. The peptide nucleic acid monomer of claim 1, wherein the nucleobase is a purine base or a pyrimidine base.

\* \* \* \* \*